(12) United States Patent
Mathad et al.

(10) Patent No.: US 8,969,623 B2
(45) Date of Patent: *Mar. 3, 2015

(54) METHOD FOR THE PREPARATION OF CINACALCET AND INTERMEDIATES AND IMPURITIES THEREOF

(71) Applicants: Amneal Pharmaceuticals, LLC, Bridgewater, NJ (US); Megafine Pharma (P) Ltd., Maharashtra (IN)

(72) Inventors: Vijayavitthal Thippannachar Mathad, Maharashtra (IN); Navnath Chintaman Niphade, Maharashtra (IN); Gorakshanath Balasaheb Shinde, Maharashtra (IN); Sharad Subhash Ippar, Maharashtra (IN); Shrikant Prataprao Deshmukh, Maharashtra (IN); Raghavendra Kumar Panchangam, Maharashtra (IN)

(73) Assignee: Amneal Pharmaceuticals, LLC, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/052,116

(22) Filed: Oct. 11, 2013

(65) Prior Publication Data

US 2014/0081048 A1   Mar. 20, 2014

Related U.S. Application Data

(63) Continuation of application No. 13/226,061, filed on Sep. 6, 2011, now Pat. No. 8,575,395, which is a continuation of application No. PCT/IN2009/000557, filed on Oct. 8, 2009.

(30) Foreign Application Priority Data

Mar. 9, 2009   (IN) .......................... 516/MUM/2009

(51) Int. Cl.
| | |
|---|---|
| C07C 209/00 | (2006.01) |
| C07C 209/62 | (2006.01) |
| C07C 209/86 | (2006.01) |
| C07C 211/08 | (2006.01) |
| C07C 249/02 | (2006.01) |
| C07C 251/30 | (2006.01) |
| C07C 211/30 | (2006.01) |
| C07C 251/16 | (2006.01) |
| C07C 251/24 | (2006.01) |
| C07C 251/06 | (2006.01) |

(52) U.S. Cl.
CPC ............ *C07C 209/62* (2013.01); *C07C 211/30* (2013.01); *C07C 251/16* (2013.01); *C07C 251/24* (2013.01); *C07C 251/30* (2013.01); *C07C 249/02* (2013.01); *C07C 251/06* (2013.01); *C07B 2200/07* (2013.01)
USPC .......................... 564/374; 564/270; 564/377

(58) Field of Classification Search
USPC ......................... 564/270, 374, 377
See application file for complete search history.

(56) References Cited

U.S. PATENT DOCUMENTS

| | | | |
|---|---|---|---|
| 4,966,988 | A | 10/1990 | Schinski et al. |
| 6,211,244 | B1 | 4/2001 | Van Wagenen et al. |
| 7,250,533 | B2 * | 7/2007 | Lifshitz-Liron et al. ...... 564/336 |
| 8,575,395 | B2 * | 11/2013 | Mathad et al. ................ 564/374 |
| 2008/0319229 | A1 | 12/2008 | Allegrini et al. |

FOREIGN PATENT DOCUMENTS

| | | |
|---|---|---|
| EP | 1990333 | 11/2008 |
| WO | WO-2007/127445 | 11/2007 |
| WO | WO-2008/035381 | 3/2008 |
| WO | WO-2008/058235 | 5/2008 |
| WO | WO-2009/002427 | 12/2008 |

OTHER PUBLICATIONS

Gunda et al, Tetrahedron Letters, 35(3), 381-4, 1994.*
Anderson, Craig et al., "Stereoselective oxidative addition of methyl iodide to chiral cyclometallated platinum (II) compounds derived from (R)-(+)-1-(1-naphthylethylamine). Crystal structure of [PtMe{3-(R)-(C10H7)CHMeNCHC4H2S}PPh3]", *Journal of Organometallic Chemistry* 631 May 18, 2001, 164-174.
Shinde, Gorakshanath B. et al., "Industrial Application of the Forster Reaction: Novel One-Pot Synthesis of Cinacalcet Hydrochloride, a Calcimimetic Agent", *Organic Process Research & Development*, 15 2011, 455-461.
Thiel, Oliver R. et al., "Practical synthesis of the calcimimetic agent, cinacalcet", *Tetrahedron Letter*, Volume Date 2008, 49(1) 2007, 13-15.

* cited by examiner

*Primary Examiner* — Shailendra Kumar
(74) *Attorney, Agent, or Firm* — Servilla Whitney LLC

(57) ABSTRACT

A method for the preparation of Cinacalcet is disclosed comprising treating (R)-1-naphthyl ethylamine with an aromatic aldehyde to form (1R)-1-(2-naphthyl)-N-(aryl methylene) ethanamine derivative of Formula (IV), which is further treated with 1-(3-halopropyl)-3-(trifluoromethyl)benzene of Formula (V) to obtain an iminium salt of Formula (VI), followed by hydrolysis to obtain Cinacalcet free base.

19 Claims, No Drawings

METHOD FOR THE PREPARATION OF CINACALCET AND INTERMEDIATES AND IMPURITIES THEREOF

CROSS-REFERENCE TO RELATED APPLICATIONS

This application is a Continuation of U.S. application Ser. No. 13/226,061, filed Sep. 6, 2011, now U.S. Pat. No. 8,575,395, which is a Continuation-in-Part of International Application PCT/IN2009/000557, with an international filing date of Oct. 8, 2009, which claims priority to Indian Patent Application No. 516/MUM/2009, filed on Mar. 9, 2009, all of which are incorporated herein by reference in their entireties.

BACKGROUND

1. Field of the Invention

The present invention relates to a method for the preparation of N-[1(R)-(1-naphthyl)ethyl]-N-[3-[3-(trifluoromethyl)phenyl]propyl]-1-amine, Cinacalcet, and to new intermediates and impurities formed during the preparation.

2. Background of the Invention

N-[1(R)-(1-naphthyl)ethyl]-N-[3-[3-(trifluoromethyl)phenyl]propyl]-1-amine (herein "Cinacalcet" or "CNC") has a CAS number of 226256-56-0, a formula of $C_{22}H_{22}F_3N$ and the following structure:

Formula (I)

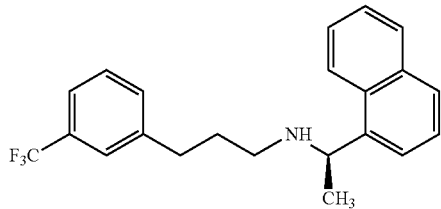

This molecule is the free base form of Cinacalcet hydrochloride (herein "CNC—HCl"), having a CAS number of 364782-34-3 and the following structure:

Formula (VII)

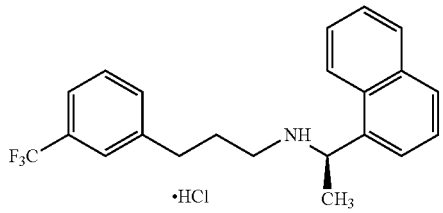

CNC—HCl is marketed as SENSIPAR™, and is the first drug in a class of compounds known as calcimimetics to be approved by the FDA.

Calcimimetics are a class of orally active, small molecules that decrease the secretion of PTH by activating calcium receptors. The secretion of PTH is normally regulated by the calcium-sensing receptor. Calcimimetic agents increase the sensitivity of this receptor to calcium, which inhibits the release of parathyroid hormone, and lowers parathyroid hormone levels within a few hours. Calcimimetics are used to treat hyperparathyroidism, a condition characterized by the oversecretion of PTH that results when calcium receptors on parathyroid glands fail to respond properly to calcium in the bloodstream. Elevated levels of parathyroid hormone (PTH), an indicator of secondary hyperparathyroidism, are associated with altered metabolism of calcium and phosphorus, bone pain, fractures, and an increased risk for cardiovascular death. As a calcimimetic, CNC—HCl is approved for treatment of secondary hyperparathyroidism in patients with chronic kidney disease on dialysis. Treatment with CNC—HCl lowers serum levels of PTH, as well as the calcium/phosphorus ion product in the blood.

U.S. Pat. No. 6,211,244 discloses calcium receptor-active compounds related to Cinacalcet and methods of making such compounds. In accordance with the patent, Cinacalcet may be produced by reacting 1-acetyl naphthalene with 3-[3-(trifluoromethyl)phenyl]propylamine in the presence of titanium isopropoxide to produce an imine corresponding to Cinacalcet, followed by treatment with methanolic sodium cyanoborohydride and resolution of the racemic Cinacalcet base by chiral liquid chromatography, according to Scheme 1:

Scheme 1

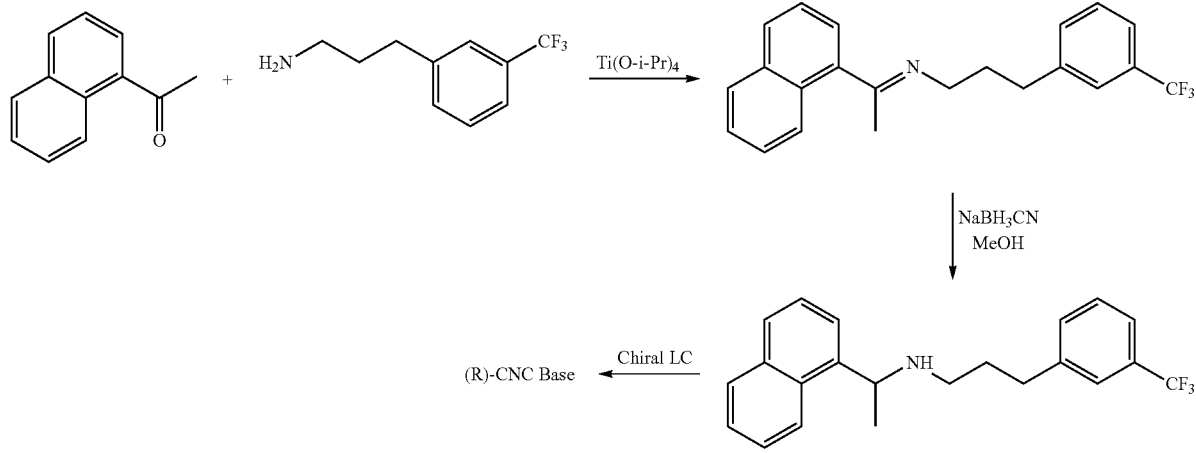

CNC base racemic

Similarly, using the process disclosed in U.S. Pat. No. 6,211,244, as well as DRUGS OF THE FUTURE (2002) 27 (9): 831 the desired Cinacalcet enantiomer may be produced by reacting (R)-1-(1-naphthyl)ethylamine with 3-[3-(trifluoromethyl)phenyl]propionaldehyde in the presence of titanium isopropoxide to produce the imine that corresponds to Cinacalcet, followed by treatment with ethanolic sodium cyanoborohydride, according to the following Scheme 2:

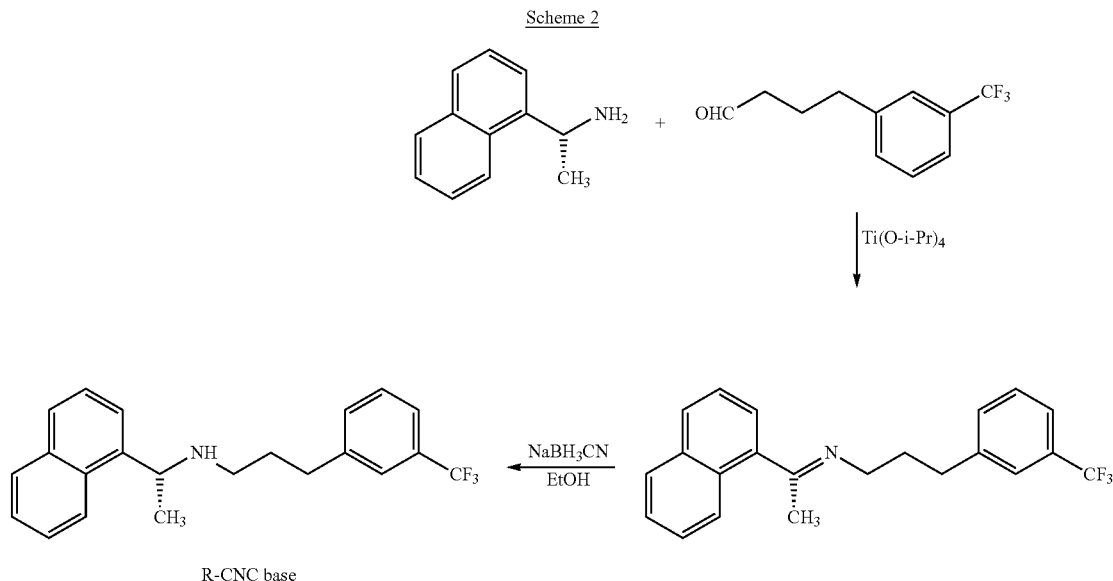

U.S. Pat. No. 6,211,244 discloses an additional process for the synthesis of Cinacalcet. This process involves treating 3-trifluoromethylcinnamonitrile, which can be prepared as disclosed in U.S. Pat. No. 4,966,988, with diisobutyl aluminum hydride, followed by treating the intermediate aluminumimine complex with (R)-1-(1-naphthyl)ethylamine, and reducing the intermediate imine with ethanolic sodium cyanoborohydride, according to the following Scheme 3:

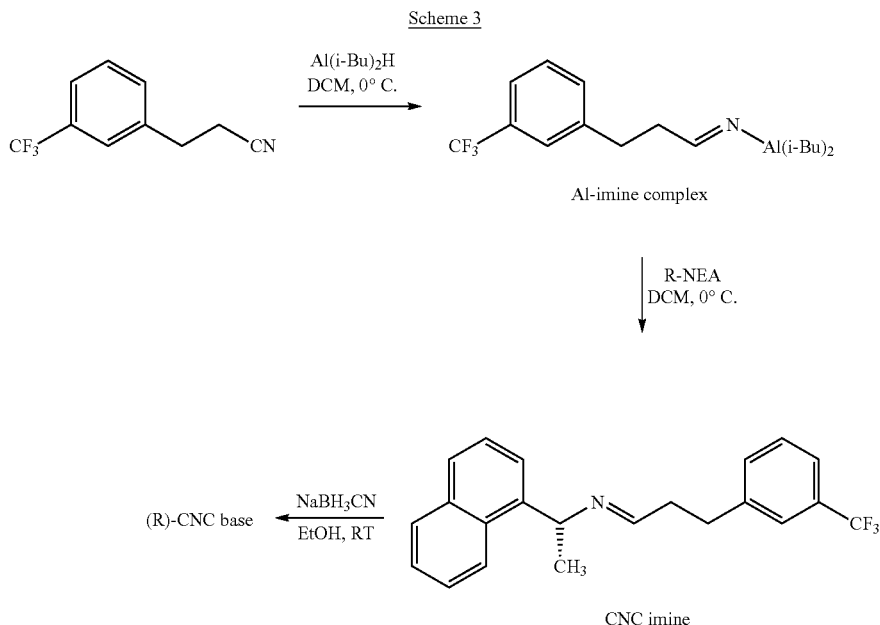

These three processes however, require the use of reagents such as titanium isopropoxide, which is highly hygroscopic and expensive, as well as toxic, and ethanolic or methanolic sodium cyanoborohydride, which is highly toxic and flammable, and not environmentally friendly, making the processes difficult to apply on industrial scale. The chiral separation method used in Scheme 1 to obtain the desired enantiomer is industrially not feasible and economically not viable. Further, losing half molecule after its complete formation is industrially, particularly economically, not viable.

Additionally, the product mixture of a chemical reaction is rarely a single compound with sufficient purity to comply with pharmaceutical standards. Side products and by-products of the reaction and adjunct reagents used in the reaction will, in most cases, also be present in the product mixture. Like any synthetic compound, Cinacalcet can contain related substances or impurities that can come from many sources. They can be unreacted starting materials, by-products of the reaction, products of side reactions, or degradation products.

Generally, impurities are identified spectroscopically and/or with another physical method, and then are associated with a peak position, such as that in a chromatogram, or with a spot on a TLC plate. Thereafter, the impurity can be identified, e.g., by its relative position in the chromatogram, where the position in a chromatogram is measure in minutes between injection of the sample on the column and elution of the particular component through the detector. The relative position in the chromatogram is known as the "retention time."

Retention time can vary about a mean value based upon the condition of the instrumentation as well as many other factors. To mitigate the effects such variations have upon accurate identification of an impurity, those skilled in the art use the "relative retention time" (RRT) to identify impurities. The RRT of an impurity is its retention time divided by the retention time of a reference marker.

One skilled in the art understands that a compound in a relatively pure state can be used as a "reference standard." The reference standard is similar to the reference marker, which is used for qualitative analysis only, but is used to quantify the amount of the compound of the reference standard in an unknown mixture as well. A reference standard is an "external standard," when a solution of a known concentration of the reference standard and an unknown mixture are analyzed using the same technique. The amount of the compound in the mixture can be determined by comparing the magnitude of the detector response.

The reference standard can also be used to quantify the amount of another compound in the mixture if a "response factor," which compensates for differences in the sensitivity of the detector to the two compounds, has been predetermined. For this purpose, the reference standard is added directly to the mixture, and is known as an "internal standard."

The management of process related impurities is enhanced by understanding their chemical structures and synthetic pathways, and by identifying the parameters that influence the amount of impurities in the final product.

Thus, an alternative process for the preparation of Cinacalcet base and Cinacalcet salt, which is direct, environmentally friendly, applicable to industrial scale production, and leading to higher yield, is desirable. Additionally, it is desirable that there is a method for identifying, quantifying and separating the impurities formed as a result of the synthesis of Cinacalcet.

SUMMARY

This invention relates to a method for the preparation of N-[1(R)-(1-naphthyl)ethyl]-N-[3-[3-(trifluoromethyl) phenyl]propyl]-1-amine, Cinacalcet, of the Formula (I);

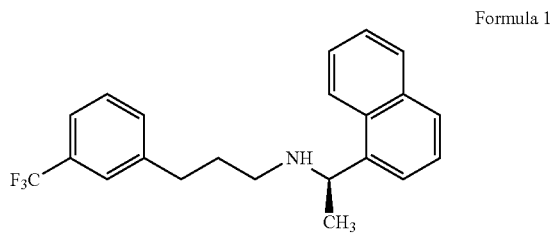 [SMILES: C[C@@H](NCCCc1cccc(C(F)(F)F)c1)c1cccc2ccccc12]

Formula 1

This invention also relates to (1R)-1-(2-naphthyl)-N-(arylmethylene)-ethanamine derivative of the Formula (IV), Formula (IV)

which is used as an intermediate for the preparation of Cinacalcet.

This invention also relates to a process for the preparation of (1R)-1-(2-naphthyl)-N-(arylmethylene)-ethan amine derivative of Formula (IV).

This invention also relates to an iminium salt of Formula (VI);

Formula (VI)

which is formed as an intermediate for the preparation of Cinacalcet.

This invention also relates to a process for the preparation of the iminium salt compound of Formula (VI) which is formed as an intermediate for the preparation of Cinacalcet.

This invention also relates to a reverse phase high performance liquid chromatography (HPLC) method of identifying and separating the impurities formed during the synthesis and preparation of Cinacalcet.

This invention also relates to five novel impurities (Impurities 7, 8, 9, 10, and 11), their identification, isolation, and characterization, formed during the synthesis and preparation of Cinacalcet.

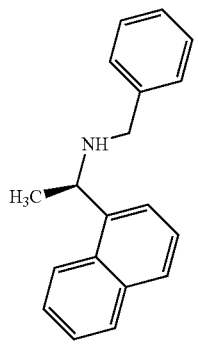

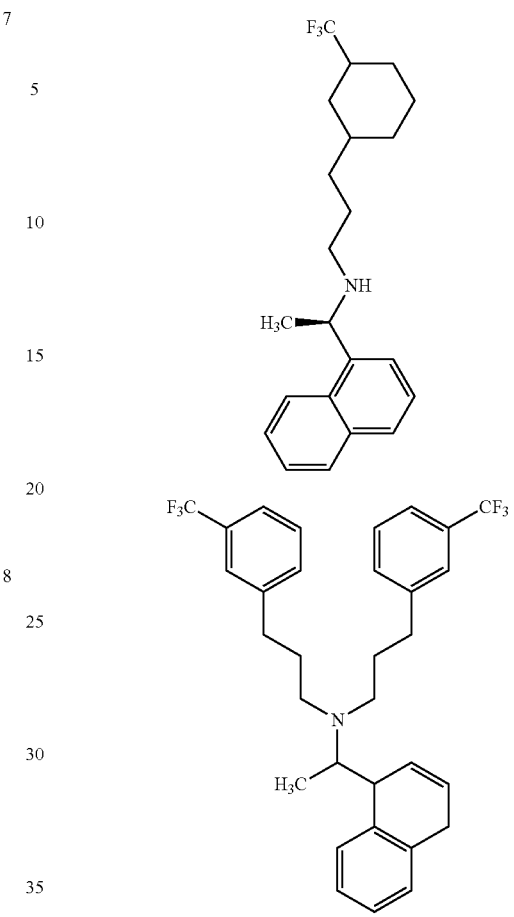

An object of the present invention is to provide a method for the preparation of Cinacalcet and/or its salts, wherein the process is simple, efficient, cost-effective, and easy to carry out. Another object of the invention is to provide a new method for the preparation of Cinacalcet base and/or its salts, which is substantially pure and free from impurities.

Yet another object of the invention is to provide a method for the preparation of Cinacalcet and/or its salts in a single pot wherein isolation of intermediates by filtrations are around time of the total time cycle per batch.

Yet another object of the invention is to provide a method for the preparation of Cinacalcet and/or its salts in which aromatic aldehyde, which is used as a starting material, may be easily and efficiently recovered and recycled from the reaction mixture, thus reducing the effluents and making the process cost-effective and eco-friendly.

Yet another object of the invention is directed toward Cinacalcet and/or its salts that is substantially free of impurities, in particular Impurities 7, 8, 9, 10, and 11.

Yet another object of the invention is directed toward a pharmaceutical preparation of Cinacalcet and/or its salts that is substantially free of impurities, in particular Impurities 7, 8, 9, 10, and 11.

DETAILED DESCRIPTION

Preparation of Cinacalcet

The present invention provides a novel method for efficiently preparing Cinacalcet and/or its pharmaceutically acceptable salts. According to the process of present invention, Cinacalcet is obtained by using milder reaction conditions and without the need for laborious operations such as chromatographic purifications or solvent distillations, and hazardous chemicals.

The process for making the compound of Formula (I) of the invention involves three steps. While the steps are normally run separately, that is consecutively, the process may nonetheless be conveniently performed in a one pot arrangement as well, e.g. as a one pot process without isolation of the intermediates.

According to the invention, there is provided a new method for the preparation of Cinacalcet of Formula (I):

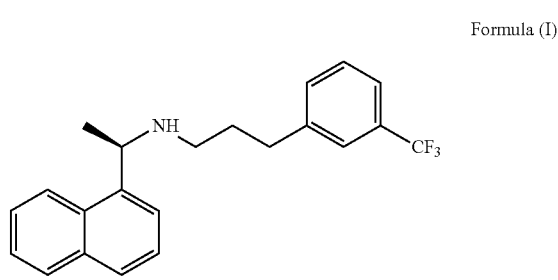 [SMILES: C[C@@H](NCCCc1cccc(C(F)(F)F)c1)c1cccc2ccccc12]

Formula (I)

the method comprising:

a. reacting (R)-1-naphthyl ethylamine of the Formula (II) and an aromatic aldehyde of Formula (III) to form (1R)-1-(2-naphthyl)-N-(aryl methylene)-ethanamine derivative of Formula (IV);

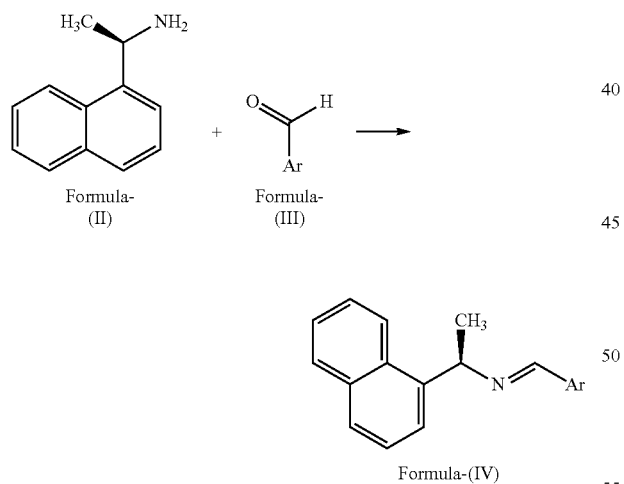

wherein,

Ar is benzyl-, phenyl- or naphthyl-, which may be mono- or di- or poly substituted with alkyl, aryl, alkoxy, amino, hydroxyl, halogen, and nitro groups.

b. treating the reaction mixture comprising (1R)-1-(2-naphthyl)-N-(arylmethylene)-ethanamine derivative of Formula (IV) which is obtained from step (a) with 1-(3-halopropyl)-3-(trifluoromethyl)benzene of Formula (V) to form an iminium salt of Formula (VI);

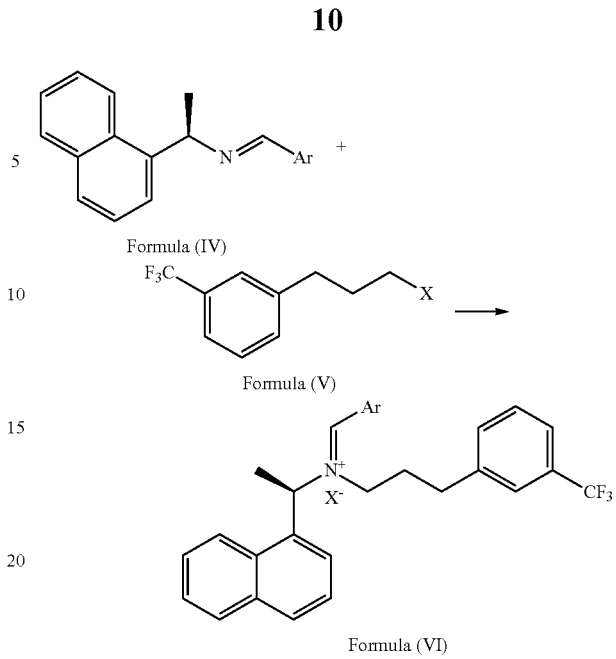

wherein,

Ar is benzyl-, phenyl- or naphthyl-, which may be mono- or di- or poly substituted with alkyl, aryl, alkoxy, amino, hydroxyl, halogen, and nitro groups, and
X is chloro, bromo or iodo
and c. treating the reaction mixture of step (b) comprising iminium salt of Formula (VI) with water and/or acid solution to obtain Cinacalcet free base of the Formula (I).

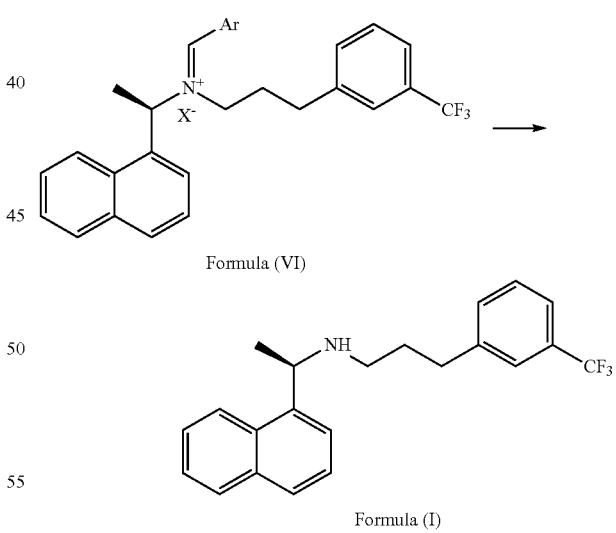

wherein,

Ar is benzyl-, phenyl- or naphthyl-, which may be mono- or di- or poly substituted with alkyl, aryl, alkoxy, amino, hydroxyl, halogen, and nitro groups, and
X is chloro, bromo or iodo.

According to the one of the embodiments of the invention, step (a) of the above-mentioned method comprises reacting (R)-1-naphthyl ethylamine of Formula (II) and aromatic aldehyde of Formula (III) at temperature of 10 to 150° C.

Preferably, step (a) of the above-mentioned method is carried out without solvent at temperature of 10 to 45° C.; more preferably the step (a) is carried out at temperature of 25 to 35° C.

According to another embodiment of the invention, step (a) of the above-mentioned method optionally comprises reacting (R)-1-naphthyl ethylamine of Formula (II) and aromatic aldehyde of Formula (III) at temperature of 60 to 150° C. in the presence of solvent. Preferably, step (a) is carried out in the presence of solvent at temperature of 60 to 125° C., more preferably, 80 to 120° C.

Aromatic aldehyde used in step (a) of the above-mentioned method may be selected from benzyl-, phenyl- or naphthyl- which may be mono- or di- or poly-substituted with alkyl, aryl, alkoxy, amino, hydroxyl, halogen, or nitro groups. The aldehyde used in step (a) is selected from benzaldehyde, salisaldehyde, hydroxyl benzaldehyde, o-chlorobenzaldehyde, p-methoxy benzaldehyde, o-methoxy benzaldehyde, p-nitrobenzaldehyde and mixtures thereof. Preferably, the aromatic aldehyde used in step (a) is benzaldehyde.

The solvent used in step (a) of the above-mentioned method is selected from organic solvents and/or inorganic solvents or mixtures thereof.

The organic solvents used in step (a) of the above-mentioned method may be selected from the group consisting of a hydrocarbons, alcohols, $C_1$-$C_{10}$ ether, $C_5$-$C_8$ cyclic ether, $C_2$-$C_{10}$ aliphatic ester, $C_2$-$C_8$ aliphatic amides, cyclic amides, sulfoxide, $C_1$-$C_8$ chlorinated hydrocarbon, and mixtures thereof. Particularly, the solvent is selected from alcohols such as methanol, ethanol, propanol, butanol and the like, hydrocarbons such as toluene, xylene and the like, and mixture thereof; more preferably, the solvent is toluene or ethanol.

The inorganic solvents used in step (a) of the above-mentioned method may be ionic liquids selected from 1-ethyl-3-methyl imidazolium ethylsulfate, [hmim]BF4, [hbim]Br, [hbim]Cl, [hbim]BF4, [hbim]PF6, [bbim]Br, [bbim]Cl, [bbim]ClO4, [bbim]BF4, [bmim]PF6, [bmim]BF4, and the like, and mixtures thereof.

The reaction time of step (a) of the above-mentioned method invariably depends on the temperature condition used to carry out step (a). The reaction time increases with decrease in temperature. The course of the reaction is monitored by a suitable analytical method, for instance by TLC or HPLC till the completion of the reaction.

Step (a) of the above-mentioned method further/optionally comprises isolating (1R)-1-(2-naphthyl)-N-(arylmethylene)-ethanamine derivative of Formula (IV) as a white crystalline solid by filtering the reaction mass of step (a).

According to one of the embodiments of the invention, the above mentioned step (b) comprises treating the reaction mixture of step (a) comprising (1R)-1-(2-naphthyl)-N(arylmethylene)ethanamine derivative of Formula (IV) with 1-(3-halopropyl)-3-(trifluoromethyl)benzene of Formula (V) at a temperature of 80-180° C. to form an iminium salt of Formula (VI).

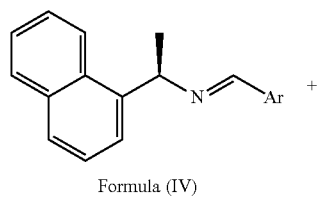

Formula (IV)

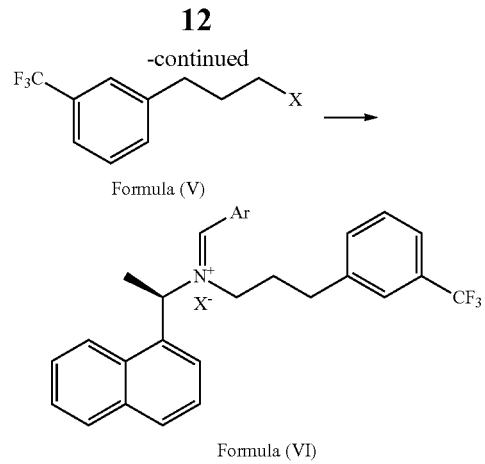

wherein,
Ar is benzyl-, phenyl- or naphthyl-, which may be mono- or di- or poly substituted with alkyl, aryl, alkoxy, amino, hydroxyl, halogen, and nitro groups, and
X is chloro, bromo or iodo.

In another embodiment of the invention, step (b) of the above-mentioned method optionally comprises treating the reaction mixture of step (a) comprising (1R)-1-(2-naphthyl)-N-(arylmethylene)-ethanamine derivative of Formula (IV) with 1-(3-halopropyl)-3-(trifluoromethyl)benzene of Formula (V) at temperature of 80-180° C. in the presence of a solvent.

In yet another embodiment of the invention, the above mentioned step (b) optionally comprises treating the (1R)-1-(2-naphthyl)-N-(arylmethylene)-ethanamine derivative of Formula (IV) as isolated from step (a) with 1-(3-halopropyl)-3-(trifluoromethyl)benzene of Formula (V) at temperature of 80-180° C. to obtain iminium salt of the Formula (VI).

In yet another embodiment of the invention, the above mentioned step (b) further comprises treating the (1R)-1-(2-naphthyl)-N-(arylmethylene)ethanamine derivative of Formula (IV) as isolated from step (a) with 1-(3-halopropyl)-3-(trifluoromethyl)benzene of Formula (V) at temperature of 80-180° C. optionally in the presence of a solvent to obtain iminium salt of Formula (VI).

Preferably, step (b) of the above-mentioned method is carried out in the presence of solvent.

Preferably, step (b) of the above-mentioned method is carried out at reflux temperature of the solvent which is used in the step (b).

The solvent used in step (b) of the above-mentioned method is selected from organic solvent and/or inorganic solvent and mixtures thereof.

The organic solvent may be selected from $C_2$-$C_8$ aliphatic amides including but not limited to N,N-dimethylacetamide, dimethylformamide, hexamethylphosphoramide and the like, cyclic amides including but not limited to 1,3-dimethyl-2-imidazolidinone (DMI), N-methyl-2-pyrrolidinone (NMP) and the like; dimethylsulfoxides; hydrocarbon solvents including but not limited to toluene, xylene, and the like; alcoholic solvents including but not limited to methanol, ethanol, propanol, butanol, and the like; ether solvent including not limited to diglymes; and mixtures thereof. Preferably, the organic solvent used in the step (b) of the above-mentioned reaction is N-methyl-2-pyrrolidinone.

The inorganic solvents used in step (b) of the above-mentioned method may be ionic liquids selected from 1-ethyl-3-methyl imidazolium ethylsulfate, [hmim]BF4, [hbim]Br,

[hbim]Cl, [hbim]BF4, [hbim]PF6, [bbim]Br, [bbim]Cl, [bbim]ClO4, [bbim]BF4, [bmim]PF6, [bmim]BF4, and the like and mixtures thereof.

A catalyst may be used in step (b) of the above-mentioned method can be selected from potassium iodide (KI), sodium iodide (NaI) or phase transfer catalysts such as n-benzylcinchonidinium chloride, benzyltributylammonium chloride, 3-ethyl-5-(2-hydroxyethyl)-4-methylthiazolium bromide, phenyltrimethylammonium chloride, tetrabutylammonium bromide, tetrabutylammonium chloride, tricaprylmethylammonium chloride, tetrabutylammonium iodide and the like or combinations thereof.

Step (b) of the above-mentioned method is carried at 80-180° C.; preferably, step (b) is carried out at 120 to 150° C.

1-(3-halopropyl)-3-(trifluoromethyl)benzene of Formula (V) is selected from 1-(3-chloropropyl)-3-(trifluoromethyl)benzene, 1-(3-bromopropyl)-3-(trifluoromethyl)benzene or 1-(3-iodopropyl)-3-(trifluoromethyl)benzene.

According to one of the embodiments of the invention, step (c) of the above mentioned method comprises treating (i.e. hydrolyzing) the reaction mixture of step (b) comprising iminium salt of Formula (VI) with water and/or acid solution at temperature of 20-60° C. to obtain Cinacalcet free base of the Formula (I).

The acid solution used for hydrolysis of the iminium salt of the Formula (VI) may be concentrated hydrochloric acid.

Preferably, the hydrolysis of iminium salt of Formula (VI) is carried out by using water.

Step (c) of the above-mentioned method is carried out till the completion of hydrolysis which is monitored by simple thin layer chromatography.

Step (c) of the above-mentioned method may further comprise isolation of compound of Formula (I) by
  I. cooling the reaction mass of step (c) followed by diluting it with water and a water immiscible organic solvent;
  II. basifying the reaction mixture obtained from step (I) to adjust the pH to 9-10 using a suitable base, including but not limited to aqueous ammonia, sodium hydroxide, potassium hydroxide, and the like;
  III. separating the organic layer comprising Cinacalcet, (1R)-1-naphthyl ethylamine and benzaldehyde by retaining 1-(3-halopropyl)-3-(trifluoromethyl)benzene of Formula (V) in the aqueous layer;
  IV. washing the organic layer with water;
  V. washing the organic layer with a 10% solution of sodium meta-bisulphite to remove the benzaldehyde from the organic layer in the form of adduct;
  VI. diluting the organic layer with water followed by adjusting the pH of the reaction mass to 1-5 using acid, which may be organic or inorganic, including but not limited to, hydrochloric acid, sulfuric acid, nitric acid, acetic acid, formic acid and the like;
  VII. separating the organic layer comprising Cinacalcet salt by leaving the (1R)-1-naphthyl ethylamine salt in the aqueous layer, which can be recovered easily;
  VIII. washing the organic layer containing Cinacalcet salt with water followed by adjusting the pH of the layer to 8-10 using suitable base, including but not limited to, aqueous ammonia, sodium hydroxide, potassium hydroxide, and the like; and
  IX. separating the organic layer containing Cinacalcet base followed by concentrating the layer either by distillation or by evaporation to isolate Cinacalcet base.

The water immiscible organic solvent used in step (I) of the above-mentioned method is selected from hydrocarbon including benzene, toluene, xylene, heptane, hexanes, cyclohexanes and the like; esters such as ethylacetate, isobutylacetate, methylacetate and the like; ethers such as diethylether, dimethylether, ethylmethylether, isobutylether, methyl-tertbutylether and the like; chlorinated hydrocarbons such as chloroform, dichloromethane and the like; and mixtures thereof. Preferably, the water immiscible organic solvent used is toluene.

The aqueous layer comprising benzaldehyde in the form of metabisulphite adduct separated in step (V) of the above-mentioned method is removed and recovered by treating it with formaldehyde solution followed by extracting with water immiscible solvent, such as toluene, xylene, hexane, heptane, dichloromethane and the like, and concentrating the organic layer to give benzaldehyde, which can be recycled in the process to improve the economy of the process and to reduce the effluent load.

The aqueous layer comprising (1R)-(1-naphthyl)ethylamine separated in step (VII) of the above-mentioned method is recovered by basifying the layer using suitable base, such as aqueous ammonia, sodium hydroxide, potassium hydroxide, and the like to adjust the pH of the reaction mixture to 8-9, extracting (1R)-(1-naphthyl)ethylamine in water immiscible solvent, such as toluene, xylene, hexane, heptane, dichloromethane, ethylacetate and the like or chlorohydrocarbons such as dichloromethane, chloroform and the like, and evaporating the solvent to give pure (1R)-1-naphthyl ethylamine, which can be reused to improve the cost and efficiency the process.

The compound of the Formula (I) may be treated with a suitable acid to convert it into pharmaceutically acceptable salts in suitable solvents.

The suitable solvents used to prepare salts of the compound of Formula (I) are selected from hydrocarbon including benzene, toluene, xylene, heptane, hexanes, cyclohexanes and the like; esters such as ethylacetate, isobutylacetate, methylacetate, isopropylacetate and the like; ethers such as diethylether, dimethylether, ethylmethylether, isobutylether, methyl-tert-butylether and the like; chlorinated hydrocarbons such as chloroform, dichloromethane and the like; alcoholic solvent including but not limited to methanol, ethanol, propanol, butanol and the like; ketonic solvent including but not limited to acetone, methylisobutylketone, tert-butylketone and the like; water; acetonitrile; and mixtures thereof.

In another embodiment of the invention, Cinacalcet is converted into its pharmaceutically acceptable salts without isolating the Cinacalcet base of Formula (I).

In one of the embodiments of the invention, Cinacalcet hydrochloride of Formula (VII) is prepared without isolating Cinacalcet base of Formula (I) by
  a. diluting the organic layer obtained from step (V) of step (c) of the above-mentioned method with water followed by adjusting the pH of the reaction mass to 1-5 using hydrochloric acid;
  b. separating the organic layer comprising Cinacalcet hydrochloride salt of Formula (VII) from the step (a) by retaining (1R)-1-naphthyl ethylamine salt in aqueous layer, which can be recovered easily;
  c. washing the organic layer containing Cinacalcet hydrochloride salt of Formula (VII) with water followed by concentrating the organic layer to give Cinacalcet hydrochloride of Formula (VII) as a thick syrup;
  d. diluting the thick syrup obtained in the step (c) with the organic solvent, stifling the mixture and isolating the Cinacalcet hydrochloride by filtration; and
  e. purifying the Cinacalcet hydrochloride of Formula (VII) by contacting it with organic solvent, stifling the resulting mixture to 55-60° C., cooling to 10-15° C. and isolating the Cinacalcet hydrochloride of Formula (VII) by filtration.

The organic solvent used in step (d) of the above-mentioned method is selected from hydrocarbon including benzene, toluene, xylene, heptane, hexanes, cyclohexanes and the like; ethers such as diethylether, dimethylether, ethylmethylether, isobutylether, diisopropylether, methyl-tert-butylether and the like; chlorinated hydrocarbons such as chloroform, dichloromethane, dichloroethane and the like; and mixtures thereof. Preferably, the solvent used to isolate salt of compound of Formula (I) in step (d) is diisopropylether.

The organic solvent used in step (e) of the above-mentioned method is selected from esters such as ethyl acetate, isobutyl acetate, methyl acetate, isopropyl acetate and the like; alcoholic solvent including but not limited to methanol, ethanol, propanol, butanol and the like; ketonic solvent including but not limited to acetone, methylisobutylketone, tert-butylketone and the like; nitriles such as acetonitrile and the like; and mixtures thereof. Preferably, the solvent used for purifying the salt of compound of Formula (I) in step (e) is ethyl acetate.

The organic layer comprising exclusively Cinacalcet hydrochloride of Formula (VII) separated in step (b) of the above-mentioned method is isolated by washing the organic layer with water to remove traces of (1R)-1-naphthyl ethylamine and distilling out the solvent from the organic layer under vacuum to give a thick syrup. In step (d) the syrup is diluted with diisopropylether with stirring for 6-8 hours and isolating the Cinacalcet hydrochloride by filtration.

In step (e) of the above-mentioned method, the wet Cinacalcet hydrochloride of Formula (VII) is contacted or suspended in ethyl acetate at 55-60° C., cooled to 10-15° C., isolated by filtration, and dried at 50-55° C. for 4 hours.

Optionally, the Cinacalcet hydrochloride obtained in the step (e) of the above-mentioned method is recrystallized by dissolving it in a mixture of organic solvent and water at 60-65° C., cooling the solution to 15-20° C., isolating the pure Cinacalcet hydrochloride by filtration and drying the Cinacalcet hydrochloride at 50-55° C. for 6 hours.

The mixture of organic solvent and water is used in the proportion of 5:95 (v/v) to 50:50 (v/v), preferably 10:90 (v/v) to 25:75 (v/v), more preferably 15:85 (v/v).

The suitable organic solvent used for recrystallization of the Cinacalcet hydrochloride is selected from alcoholic solvent including but not limited to methanol, ethanol, propanol, butanol and the like; nitriles such as acetonitrile and the like; water; and mixtures thereof.

Preferably, the solvent used in recrystallization of Cinacalcet hydrochloride is mixture of acetonitrile and water in the proportion of 15:85 (v/v).

The preferred salt of Cinacalcet base of Formula (I) is Cinacalcet hydrochloride of the Formula (VII);

Formula (VII)

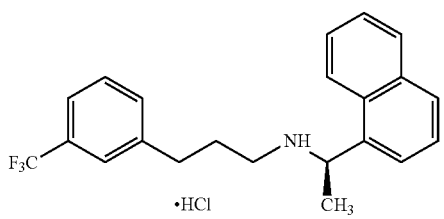

According to the present invention, overall yield of Cinacalcet hydrochloride of the Formula (VII) obtained by the above-mentioned method is greater than 50%, e.g., 52.10%, and it has purity of 99.85%.

According to the invention, there is provided the compound, (1R)-1-(2-naphthyl)-N-(arylmethylene)ethanamine, of Formula (IV);

Formula (IV)

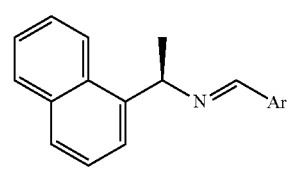

wherein Ar is benzyl-, phenyl- or naphthyl-, which may be mono- or di- or poly substituted with alkyl, aryl, alkoxy, amino, hydroxyl, halogen, and nitro groups,
which is used as intermediate for the production of Cinacalcet.

According to the invention, there is provided a process for the preparation of the compound, (1R)-1-(2-naphthyl)-N-(arylmethylene)-ethanamine, of Formula (IV), which is used as intermediate for the production of Cinacalcet; the method comprising:
a. reacting (R)-1-naphthyl ethylamine of the Formula (II) and aromatic aldehyde of Formula (III) to form (1R)-1-(2-naphthyl)-N-(arylmethylene)ethanamine derivative of Formula (IV);

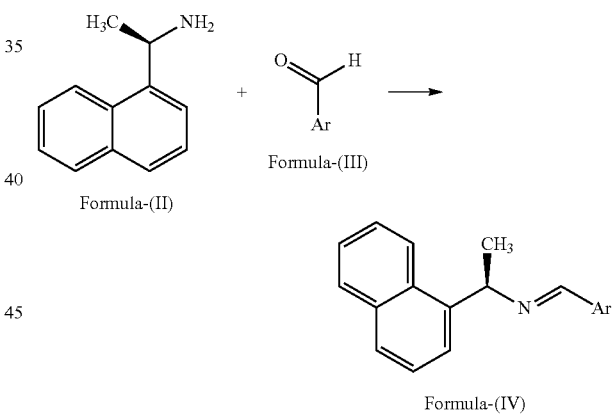

wherein,
Ar is benzyl-, phenyl- or naphthyl-, which may be mono- or di- or poly substituted with alkyl, aryl, alkoxy, amino, hydroxyl, halogen, and nitro groups
and
b. isolating (1R)-1-(2-naphthyl)-N-(arylmethylene)ethanamine derivative of formula (IV) as white crystalline solid by filtering the reaction mass of step (a).

In one of the embodiments of the invention, step (a) of the above-mentioned method comprises reacting (R)-1-naphthyl ethylamine of Formula (II) and aromatic aldehyde of formula (III) at temperature of 10 to 150° C.

Preferably, step (a) of the above-mentioned method is carried out without solvent at temperature of 10 to 45° C. More preferably step (a) is carried out at temperature of 25-35° C.

According to another embodiment of the invention, step (a) of the above-mentioned method optionally comprises reacting (R)-1-naphthyl ethylamine of Formula (II) and aromatic aldehyde of Formula (III) at temperature of 60 to 150° C. in the presence of solvent. Preferably, step (a) is carried out in the presence of solvent at temperature of 60 to 125° C., more preferably, 80 to 120° C.

The aromatic aldehyde used in step (a) of the above-mentioned method may be selected from benzyl-, phenyl- or naphthyl, which may be mono- or di- or poly-substituted with alkyl, aryl, alkoxy, amino, hydroxyl, halogen, and nitro groups. The aldehydes used in step (a) may be benzaldehyde, salisaldehyde, p-hydroxy benzaldehyde, o-chlorobenzaldehyde, p-methoxy benzaldehyde, o-methoxy benzaldehyde, p-nitrobenzaldehyde and mixtures thereof. Preferably, the aromatic aldehyde used in step (a) is benzaldehyde.

The solvent used in step (a) of the above-mentioned method is selected from organic solvent and/or inorganic solvent and mixtures thereof;

The organic solvents used in step (a) of the above-mentioned method are selected from the group consisting of a hydrocarbons, alcohols, $C_1$-$C_{10}$ ether, $C_5$-$C_8$ cyclic ether, $C_2$-$C_{10}$ aliphatic ester, $C_2$-$C_8$ aliphatic amides, sulfoxide, $C_1$-$C_8$ chlorinated hydrocarbon, and mixtures of thereof. Particularly, the solvent is selected from alcohols such as methanol, ethanol, propanol, butanol and the like; hydrocarbons such as toluene, xylene and the like; and mixtures thereof. Preferably, the solvent is toluene or ethanol.

The inorganic liquids may be ionic liquids selected from 1-ethyl-3-methyl imidazolium ethylsulfate, [hmim]BF4, [hbim]Br, [hbim]Cl, [hbim]BF4, [hbim]PF6, [bbim]Br, [bbim]Cl, [bbim]ClO4, [bbim]BF4, [bmim]PF6, [bmim] BF4, and the like, and mixtures thereof.

The reaction time of step (a) of the above-mentioned method invariably depends on the temperature condition used to carry out step (a). The reaction time increases with decrease in temperature. The course of the reaction is monitored by a suitable analytical method, for instance by TLC/HPLC until the completion of the reaction.

According to the invention, there is provided an iminium salt compound of Formula (VI);

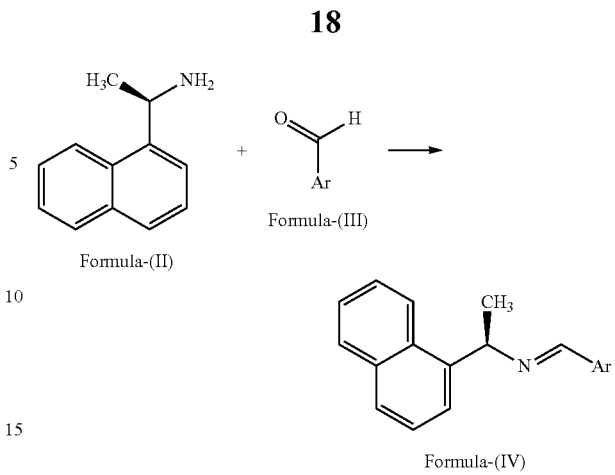

which is formed as an intermediate for the preparation of Cinacalcet. The compound of Formula (VI) may be provided in substantially pure form as defined below.

According to the invention, there is provided a process for the preparation of the iminium salt of Formula (VI), which is formed as an intermediate for the preparation of Cinacalcet; the method comprising:

a. reacting (R)-1-naphthyl ethylamine of the Formula (II) and aromatic aldehyde of Formula (III) to form (1R)-1-(2-naphthyl)-N-(arylmethylene)-ethanamine derivative of Formula (IV);

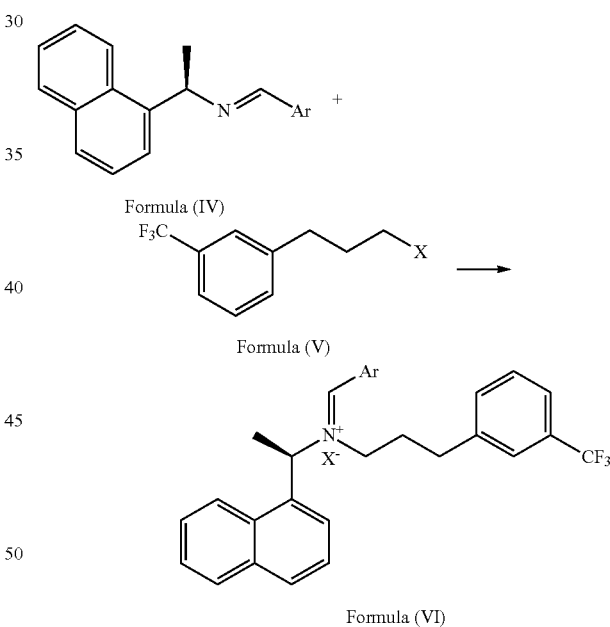

wherein,
Ar is benzyl-, phenyl- or naphthyl-, which may be mono- or di- or poly substituted with alkyl, aryl, alkoxy, amino, hydroxyl, halogen, and nitro groups
and b. treating the reaction mixture comprising (1R)-1-(2-naphthyl)-N-(arylmethylene)-ethanamine derivative of Formula (IV) which is obtained from step (a) with 1-(3-halopropyl)-3-(trifluoromethyl)benzene of Formula (V) to form iminium salt compound of Formula (VI).

wherein
Ar is benzyl-, phenyl- or naphthyl-, which may be mono- or di- or poly substituted with alkyl, aryl, alkoxy, amino, hydroxyl, halogen, and nitro groups, and
X is chloro, bromo or iodo.

In one of the embodiments of the invention, step (a) of the above-mentioned method comprises reacting (R)-1-naphthyl ethylamine of Formula (II) and aromatic aldehyde of Formula (III) at temperature of 10 to 150° C. Preferably, step (a) is carried out without solvent at temperature of 10-45° C.; more preferably at 25 to 35° C.

According to another embodiment of the invention, step (a) of the above-mentioned method optionally comprises reacting (R)-1-naphthyl ethylamine of Formula (II) and aromatic aldehyde of Formula (III) at temperature of 60 to 150° C. in the presence of solvent. Preferably, step (a) is carried out in the presence of solvent at temperature of 60 to 125° C., more preferably, 80 to 120° C.

Aromatic aldehyde used in step (a) of the above-mentioned method may be selected from benzyl-, phenyl- or naphthyl-, which may be mono- or di- or poly substituted with alkyl, aryl, alkoxy, amino, hydroxyl, halogen, and nitro groups. The aldehydes used in step (a) may be benzaldehyde, salisaldehyde, p-hydroxy benzaldehyde, o-chlorobenzaldehyde, p-methoxy benzaldehyde, o-methoxy benzaldehyde, nitrobenzaldehyde and mixtures thereof. Preferably, the aromatic aldehyde used in step (a) is benzaldehyde.

The solvent used in step (a) is selected from organic solvent and/or inorganic solvent and mixtures thereof.

The organic solvent used in step (a) of the above-mentioned method may be selected from the group consisting of a hydrocarbons, alcohols, $C_1$-$C_{10}$ ether, $C_5$-$C_8$ cyclic ether, $C_2$-$C_{10}$ aliphatic ester, $C_2$-$C_8$ aliphatic amides, sulfoxide, $C_1$-$C_8$ chlorinated hydrocarbon, and mixtures thereof. Particularly, the solvent is selected from alcohols such as methanol, ethanol, propanol, butanol and the like, hydrocarbons such as toluene, xylene and the like, and mixtures thereof. More preferably, the solvent is toluene or ethanol.

The inorganic solvent used in step (a) of the above-mentioned method may be ionic liquids selected from 1-ethyl-3-methyl imidazolium ethylsulfate, [hmim]BF4, [hbim]Br, [hbim]Cl, [hbim]BF4, [hbim]PF6, [bbim]Br, [bbim]Cl, [bbim]ClO4, [bbim]BF4, [bmim]PF6, [bmim]BF4, and the like, and mixtures thereof.

The reaction time of step (a) of the above-mentioned method is invariably depends on the temperature condition used to carry out step (a). The reaction time increases with decrease in temperature. The course of the reaction is monitored by a suitable analytical method, for instance by TLC until the completion of the reaction.

Step (a) of the above-mentioned method may further/optionally comprise isolating (1R)-1-(2-naphthyl)-N-(arylmethylene)-ethanamine derivative of Formula (IV) as a white crystalline solid by filtering the reaction mass of step (a).

According to one of the embodiments of the invention, step (b) of the above-mentioned method comprises treating the reaction mixture of step (a) comprising (1R)-1-(2-naphthyl)-N-(arylmethylene)-ethanamine derivative of Formula (IV) with 1-(3-halopropyl)-3-(trifluoromethyl)benzene of Formula (V) at temperature of 80-180° C. to obtain an iminium salt of Formula (VI)

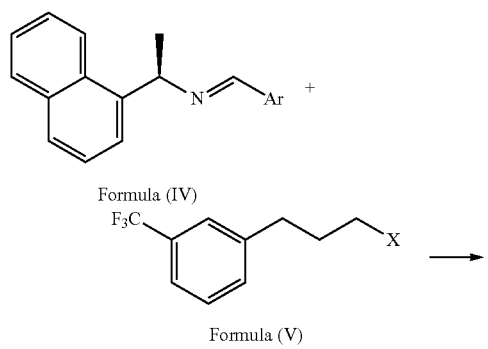

Formula (IV)

Formula (V)

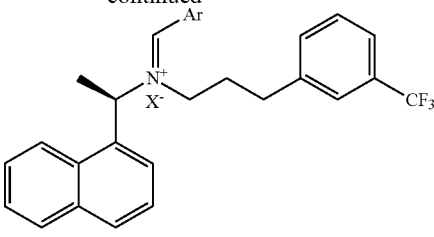

Formula (VI)

wherein

Ar is benzyl-, phenyl- or naphthyl-, which may be mono- or di- or poly substituted with alkyl, aryl, alkoxy, amino, hydroxyl, halogen, and nitro groups, and X is chloro, bromo or iodo.

In another embodiment of the invention, step (b) of the above-mentioned method optionally comprises treating the reaction mixture of step (a) comprising (1R)-1-(2-naphthyl)-N-(arylmethylene)ethanamine derivative of Formula (IV) with 1-(3-halopropyl)-3-(trifluoromethyl)benzene of Formula (V) at temperature of 80-180° C. in the presence of a solvent.

In yet another embodiment of the invention, step (b) of the above-mentioned method optionally comprises treating the (1R)-1-(2-naphthyl)-N-(arylmethylene)ethanamine derivative of Formula (IV) as isolated from step (a) with 1-(3-halopropyl)-3-(trifluoromethyl)benzene of Formula (V) at temperature of 80-180° C. to form iminium salt of the Formula (VI).

In yet another embodiment of the invention, step (b) of the above-mentioned method further comprises treating the (1R)-1-(2-naphthyl)-N-(arylmethylene)ethanamine derivative of Formula (IV) as isolated from step (a) with 1-(3-halopropyl)-3-(trifluoromethyl)benzene of Formula (V) at temperature of 80-180° C. optionally in the presence of a solvent to form iminium salt of Formula (VI).

Preferably, step (b) of the above-mentioned method is carried out in the presence of organic solvent.

Preferably, step (b) of the above-mentioned method is carried out at reflux temperature of the solvent which is used in the step (b).

The solvent used in step (b) of the above-mentioned method is selected from organic solvent and/or inorganic solvent and mixtures thereof.

The organic solvent may be selected from $C_2$-$C_8$ aliphatic amides including but not limited to N,N-dimethylacetamide, dimethylformamide, hexamethylphosphoramide and the like; cyclic amides including but not limited to 1,3-dimethyl-2-imidazolidinone (DMI), N-methyl-2-pyrrolidinone (NMP) and the like; dimethylsulfoxides; hydrocarbon solvents including but not limited to benzene, toluene, xylene, and the like; alcoholic solvents including but not limited to methanol, ethanol, propanol, butanol, and the like; ether solvent including not limited to diglymes; and mixtures thereof. Preferably, the organic solvent used in the step (b) of the above mentioned reaction is N-methyl-2-pyrrolidinone.

The inorganic solvents may be the ionic liquids selected from 1-ethyl-3-methyl imidazolium ethylsulfate, [hmim]BF4, [hbim]Br, [hbim]Cl, [hbim]BF4, [hbim]PF6, [bbim]Br, [bbim]Cl, [bbim]ClO4, [bbim]BF4, [bmim]PF6, [bmim]BF4, and the like, and mixtures thereof.

The step (b) of the above-mentioned method is carried at 80-180° C. Preferably, step (b) is carried out at 120 to 150° C.

1-(3-halopropyl)-3-(trifluoromethyl)benzene of Formula (V) may be selected from 1-(3-chloropropyl)-3-(trifluoromethyl)benzene; 1-(3-bromopropyl)-3-(trifluoromethyl)benzene or 1-(3-iodopropyl)-3-(trifluoromethyl)benzene.

The aromatic aldehyde which is used as a starting material may be easily recovered and recycled from the reaction mixture by forming an adduct with metabisulfite or any other known process which will reduce the effluents and will make the process cost-effective and eco-friendly. The present method can be carried out without isolating intermediates, thus reducing time, laborious work and cost. Thus the new method for the preparation of Cinacalcet and/or its salts is economical, simple, efficient, cost-effective and easy to carry out. According to the invention, Cinacalcet and/or its salts are obtained with high yields and substantially pure and substantially free from impurities, thus making the process efficient.

The new method for the preparation of Cinacalcet and/or its salts can be carried out in a single pot wherein isolation of intermediates by filtrations are avoided to reduce exposure of the active pharmaceutical ingredient ("API," which may also be referred to as the production executive) to chemicals and solvents, and to reduce the turnaround time of the total time cycle per batch. This invention provides compounds, (1R)-1-(2-naphthyl)-N-(arylmethylene)ethanamine, of Formula (IV) and an iminium salt compound of Formula (VI), which are used as intermediates for the production of Cinacalcet.

Process-Related Impurities from the Synthesis of Cinacalcet and RP-HPLC Method for Isolating the Impurities While developing a one-pot synthetic process for Cinacalcet hydrochloride (see above and see Scheme 4), eight process related impurities (precursors, side products formed during the reaction, reagents, impurities from starting materials, catalysts, etc.) were identified. Of these eight impurities, five novel impurities are herein described.

Evaluation (identification, characterization, and synthesis) of impurities formed during the reaction and control of the impurities in the final product to meet the regulatory norms is a critical objective during process development. As per the requirements of various regulatory authorities, the impurity profile study of drug substances and drug products has to be carried out using a suitable analytical method in the final product.

The separation of all the impurities, including degradation impurities, in a single analytical reverse phase HPLC was conducted. Analysis of the reaction mass and crude Cinacalcet hydrochloride by HPLC helped to identify the impurity peaks, which were subsequently identified by LC/MS. The impurities were synthesized, characterized, and confirmed by spiking studies using HPLC.

Scheme 5 describes the impurities identified during the synthesis of Cinacalcet using the process described herein. Alkylation of Schiff's base 4 with 5 is a very slow reaction and does not go to completion even after prolonged heating. Unreacted 4 was converted into 2 during the work-up and was selectively removed by washing the organic layer with dilute hydrochloric acid. Benzaldehyde 3 was removed by metabisulfite wash. Dimer impurity 11, formed by alkylation of 1, was eliminated by purification using ethylacetate. However, 7 that was present in a 1-2% level in the crude product was not removed. Crystallization from acetonitrile/water was established specifically to remove 7. A set of three impurities 8, 9, 10, that are formed due to the presence of impurities in 5 (5a, 5b, and 5c), were eliminated in 5. Removal of 8, 9, and 10 by recrystallization was difficult without significant yield

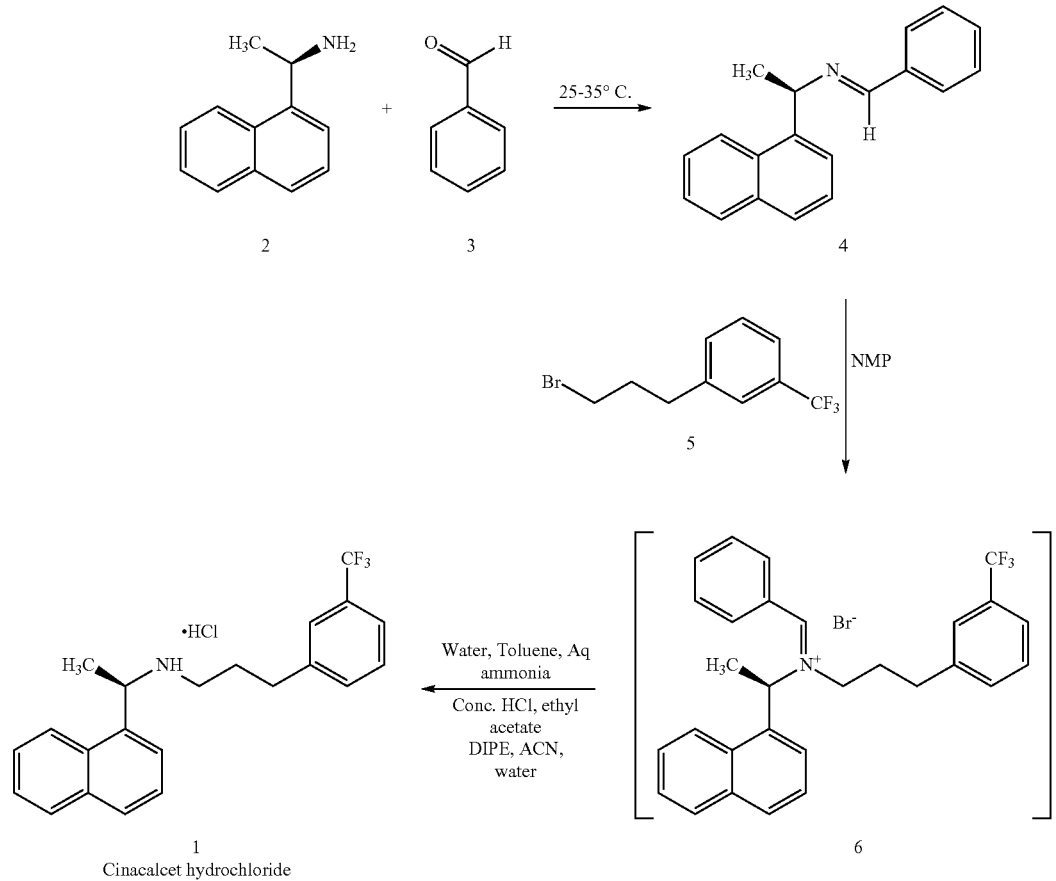

Scheme 4 loss. However, their formation during the preparation of 1 was eliminated by the purification of 5 by fractional distillation. Though the reaction condition for alkylation was harsh (130°-135° C.), racemization of the products was not observed, and chiral purity of the crude product was 99.98% by chiral HPLC.

and 11, as well as Cinacalcet 1 bulk drug and finished dosage forms substantially pure and free of one or more of impurities 5a, 5b, 5c, 7, 8, 9, 10 and 11.

A preparation of Cinacalcet 1 that is substantially pure and free of impurities was prepared. As used herein, the phrase "substantially pure and free of impurities" refers to a prepa-

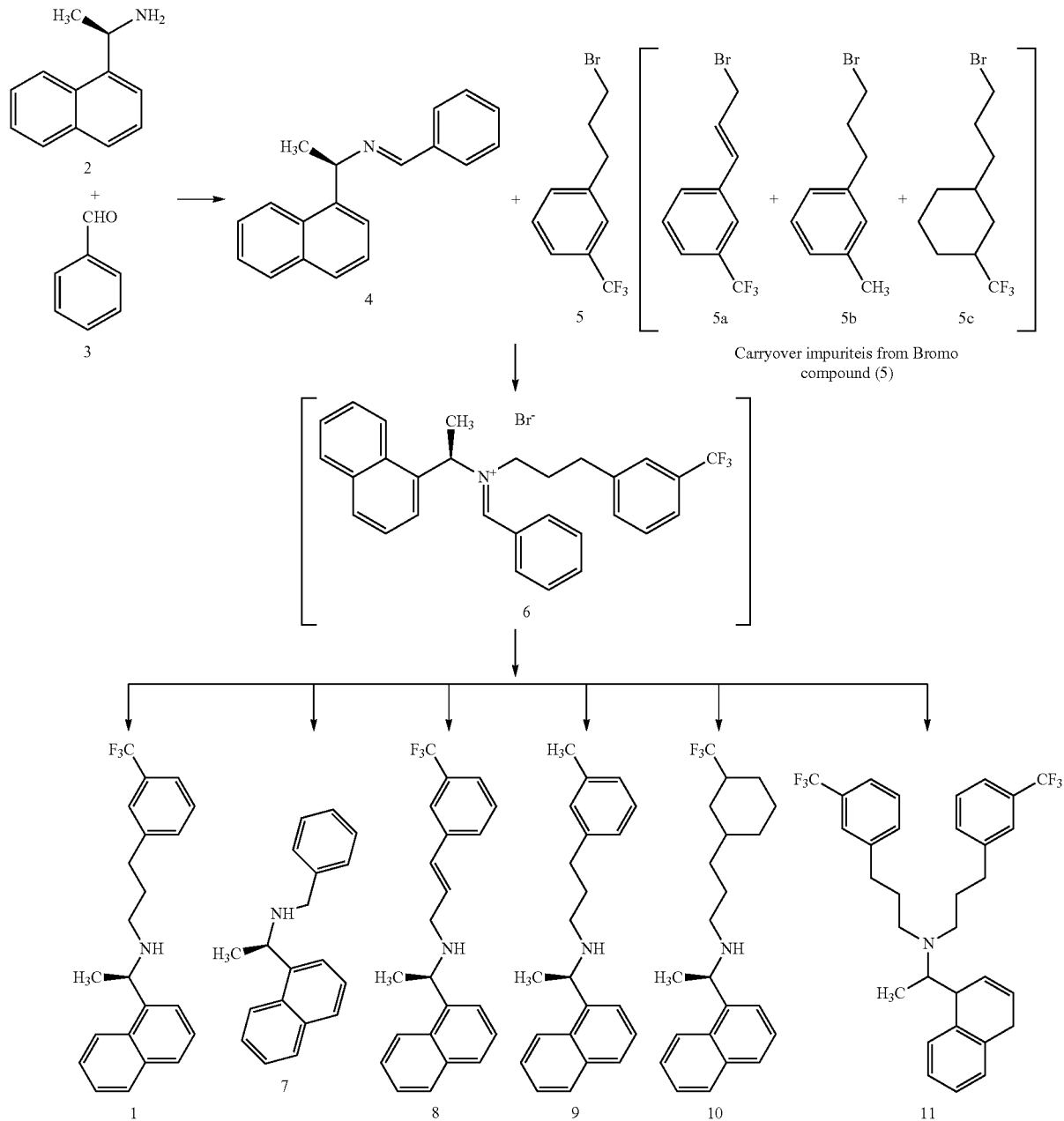

Scheme 5

Included within the scope of the invention are Cinacalcet 1 bulk drug and finished dosage forms containing detectable levels of compound 4 (IV) and/or 6 (VI), as well as Cinacalcet 1 bulk drug and finished dosage forms substantially pure and free of compound 4 and/or 6. Also included within the scope of the invention are Cinacalcet 1 bulk drug and finished dosage forms containing detectable levels of 5a, 5b, 5c, 7, 8, 9, 10 ration of Cinacalcet 1 that contains less than 0.15 percent of any impurity, based on the weight of Cinacalcet 1.

A preparation of Cinacalcet 1 was prepared that is substantially pure and free of the impurities (1R)—N-Benzyl-1-(1-naphthyl)ethanamine 7, (2E)-N-[(1R)-1-(1-Naphthyl)ethyl]-3-[3-(trifluoromethyl)phenyl]prop-2-en-1-amine 8, 3-(3-Methylphenyl)-N-[(1R)-1-(1-naphthyl)ethyl]propan-1-amine 9, 3-(3-(Trifluoromethyl)cyclohexyl)-N—((R)-1-

(naphthalene-1-yl)ethyl)propan-1-amine 10, and (1-Naphthalen-1-yl-ethyl)-N,N-bis[3-(3-trifluoromethylphenyl)-propyl]amine 11. More specifically, a preparation of Cinacalcet 1 was prepared that is substantially pure and free of impurities 8, 9, and 10. Impurities 8, 9, and 10 are formed as a result of the presence of impurities 5a, 5b, and 5c that can be present in 5. For example, as described in Scheme 6, when 5c is present during the condensation of 4 and 5, compound 4 will react with impurity 5c to form compound 6c, which leads to the formation of impurity 10.

Scheme 6

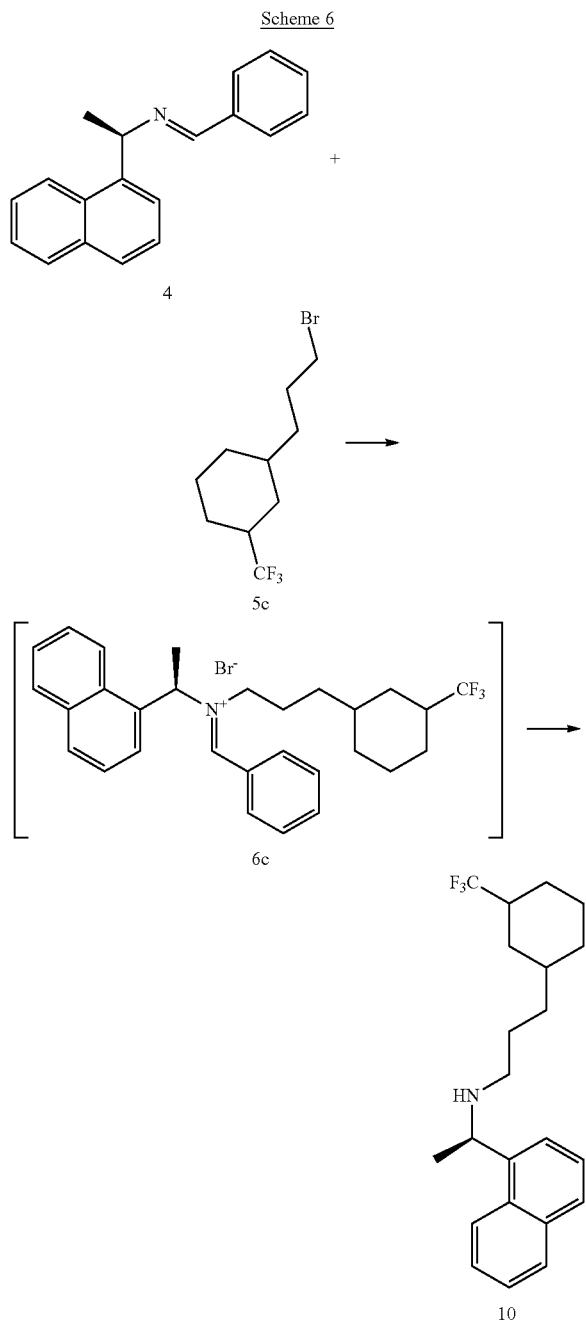

Similarly, when impurity 5b is present during the condensation of 4 and 5, impurity 8 will form; and, when impurity 5a is present during the condensation of 4 and 5, impurity 9 will form. Thus, in order to prepare Cinacalcet 1 that is substantially pure and free of impurities 8, 9, and 10, the carry-over impurities 5a, 5b, and 5c must be removed from 5 prior to condensation with 4. Removal of the impurities 5a, 5b, and 5c can be accomplished through purification of 5 by fractional distillation or other purification methods known to those skilled in the art. Therefore, when the impurities 5a, 5b, and 5c are removed from 5, Cinacalcet 1 can be prepared substantially pure and free from the impurities 8, 9, and 10. Specifically, a preparation of Cinacalcet 1 was prepared that was substantially pure and free of impurity 10; this was accomplished through the condensation of 4 and 5, wherein 5 was substantially pure and free of impurity 5c.

Cinacalcet 1 that is substantially pure and free of impurities 8, 9, and 10 (i.e. impurities 8, 9, and 10 are present in an amount of less than 0.15 percent by weight of Cinacalcet 1), may be prepared by limiting the impurities 5a, 5b, and 5c to an amount of less than 0.5 percent, preferably less than 0.15 percent by weight of 5 prior to condensation with 4.

Additionally, preparation of Cinacalcet 1 that is substantially pure and free of impurities 7 and 11 (i.e. impurities 7 and 11 are present in an amount of less than 0.5 percent by weight, preferably less than 0.15 percent of Cinacalcet 1) may be obtained by purification of Cinacalcet 1 by contacting it with organic solvent, stifling the resulting mixture to 55-60° C., cooling to 10-15° C., and isolating the Cinacalcet 1 by filtration (purification according to step (e)).

All impurities were characterized with the help of MS, FT-IR, and NMR spectroscopic techniques. The mass, FT-IR spectral date, and NMR chemical shift values of the five novel impurities are presented in the Examples.

Development of Reverse Phase HPLC Conditions

The present invention aimed to develop a chromatographic system capable of eluting and resolving Cinacalcet hydrochloride and process and degradation related impurities in a single analytical method. To establish a selective and sensitive method, the primary concern during development was to achieve symmetry of the Cinacalcet peak and resolution between the peaks of Cinacalcet and Impurity 8. Different types of buffer at different pH (e.g., phosphate buffer of pH 3-7, citrate buffer of pH 3-5, and ammonium acetate buffer of pH 4-6.5) and different columns were studied in combination with acetonitrile and methanol (30%, 50%, and 70%). The effects of acetonitrile and methanol combinations on peak height, symmetry and resolution between Cinacalcet and the impurities were investigated. The chromatographic data retention factor (k) and number of theoretical plates (N) were also recorded during these studies. Of the eight related substance impurities identified, five novel impurities were separated and determined by this chromatographic method. All impurities (related substances) were characterized using spectral data. The developed method was validated to ensure compliance in accordance with ICH guidelines. The method was found to be simple, selective, precise, accurate, and robust. Therefore, this method can be used for routine testing as well as stability analysis of Cinacalcet hydrochloride drug substance. All statistical results (percentage, mean, RSD, percentage difference and recovery %) were within the acceptance criteria. The method can be of use not only for routine evaluation of the quality of Cinacalcet hydrochloride in bulk drug manufacturing unit, but also for the detection of impurities in pharmaceutical formulations.

In yet another aspect, the present invention provides a method for determining the level of impurities in Cinacalcet comprising (a) measuring by HPLC the area under a peak corresponding to the impurity in a reference standard comprising a known amount of impurity;

(b) measuring by HPLC the area under a peak corresponding to the impurity in a sample comprising Cinacalcet and the impurity;

(c) determining the amount of the impurity in the sample by comparing the area of step (a) to the area of step (b).

Preferably, the HPLC methodology used in the above method includes the steps (a) combining a Cinacalcet sample with a mixture of water: acetonitrile in a ratio of about 50:50, to obtain a solution;

(b) injecting the solution of step (a) into a Zorbax® SB-Phenyl, 250 mm×4.6 mm, 5μ (or similar) column;

(c) eluting the sample from the column at about 50 min using a mixture of buffer:acetonitrile:methanol (45:35:20) and acetonitrile:buffer mix (80:20) as an eluent, and (d) measuring the impurity content in the relevant sample with a UV detector (preferably at 220 nm wavelength).

HPLC grade acetonitrile and methanol were used. Glacial acetic acid, hydrochloric acid, sodium hydroxide, and hydrogen peroxide were all of AR grade. HPLC grade water was used throughout the analysis.

The HPLC system of Agilent 1200 series (manufactured by Agilent Technologies) with an Agilent photodiode array detector (PDA) was used for method development, forced degradation, and method validation. The column Zorbax® SB-Phenyl, 250 mm×4.6 mm, 5μ (Agilent Technologies) thermostated at 35° C. was used for the separation. The mobile phase-A consisted of a mixture of buffer (0.1% v/v glacial acetic acid, pH 5.5 by triethylamine), acetonitrile, and methanol in a ratio of 45:35:20 v/v/v. The mobile phase-B consisted of a mixture of acetonitrile and buffer in a ratio of 80:20 v/v. The flow rate and injection volumes were 1.0 mL/min and 10 μL, respectively. The analysis was carried out under gradient conditions as follows, time (min)/A:B(v/v); $T_{0.01}$/100:0, $T_{5.0}$/100:0, $T_{10.0}$/80:20, $T_{25.0}$/20:60, $T_{35.0}$/0:100, $T_{50.0}$/0:100, $T_{53.0}$/100:0 with a post run time of 17 min. The data were acquired at 220 nm for 50 min and processed by use of Ezchrom Elite® (Agilent Technologies) data handling system. For the analysis of forced degradation samples, the photodioide array detector was used in the scan mode from 220 nm to 400 nm. The peak homogeneity was expressed in terms of peak purity values.

In yet another aspect of the present invention, a mixture of water and acetonitrile in a ratio of 50:50 (v/v) was used as the diluent in the preparation of analytical solutions. The test sample solution concentration of 1000 μg/mL was prepared for related substances (i.e. process-related impurities) determination. The individual stock solutions of all the related substances (150 μg/mL) and Cinacalcet hydrochloride (100 μg/mL) were prepared by dissolving known amount of the substances in 5 mL of acetonitrile, made up to the mark with diluent. These solutions were diluted further adequately to study the validation attributes. The specification limits used for validation studies was 0.15% for the known related substances, and 0.10% for unknown related substances. Cinacalcet hydrochloride working reference standard solution (1000 μg/mL) spiked will all impurities at a specification level (w/w) was used as a resolution mixture solution (RMS). The system suitability solution of all impurities was prepared at a specification level by diluting the above stock solutions. 10.0 μL if blank, RMS, six replicate injections of system suitability solution and test sample solution were separately chromatographed. A resolution of not less than 1.5 between Cinacalcet hydrochloride and Impurity 8 was set as a system suitability requirement in RMS. The relative standard deviation (RSD) of not more than 5.0% for all related substances peak areas obtained from six replicate injections of system suitability solution is used to verify the system precision. All the known related substances in test sample were determined against the mean area of the respective impurities obtained from replicate injections of system suitability solution. All the unknown related substances in test sample were determined against mean area of Cinacalcet obtained from replicate injections of system suitability solution.

In yet another aspect of the present invention, forced degradation of Cinacalcet hydrochloride drug substance was carried out under acid/base hydrolytic, oxidative, thermolytic, and photolytic stress conditions. Solutions were prepared by dissolving drug substance in diluents and then treating with concentrated hydrochloric acid (refluxed for 72 h), aqueous 5M sodium hydroxide (refluxed for 72 h), and aqueous 30% hydrogen peroxide (kept for 7 h at RT). After the degradation, these solutions were diluted with diluents and analyzed in the proposed method. For thermal stress, sample of drug substance was placed in a controlled temperature oven at 105° C. for 7-days. For photolytic stress, the sample was exposed in photolytic conditions for 10 days as per ICH guidelines. After the exposure to the above stress conditions, solutions of these samples were prepared by dissolving respective samples in diluents and diluted to the desired concentration and subjected for analysis using the proposed method. These stressed samples were quantified for Cinacalcet and the impurities. Photodiode array detector was employed to check and ensure the homogeneity and purity of Cinacalcet peak in all the stressed sample solutions. The assessment of mass balance in the degraded samples was carried out to confirm that the amount of impurities detected in stressed samples matched with the amount present before the stress was applied.

LC-MS analysis was carried out using triple quadrupole mass spectrometer (API 2000, PE SCIEX) coupled with a Shimadzu HPLC equipped with SPD 10A VP UV-vis detector and LC AT VP pumps. Analyst software was used for data acquisition and data processing. The turbo ion spray voltage was maintained at 5.5 kV and temperature was set at 375° C. High pure nitrogen gas was used as an auxiliary gas and curtain gas. Zero air was used as a nebulizer gas. LC-MS spectra were acquired from m/z 50 to 800 in 0.1 amu steps with 2.0 s dwell time. Cinacalcet hydrochloride crude sample was subjected to LC-MS analysis. The analysis was carried out using a reverse phase column SB-Phenyl, 250 mm×4.6 mm, 5 μm. Mobile Phase-A was containing the mixture of buffer (0.05 M ammonium acetate) and methanol in the ratio of 85:15 (v/v). The mobile phase-B was containing buffer and methanol in the ratio of 35:65 (v/v). Detection was carried out at 220 nm, and flow rate was kept at 1.0 mL/min. Water and acetonitrile mixture in the ratio of 50:50 (v/v) was used as diluents. Data acquisition time was 60 min. The gradient program was as follows: time(min)/A(v/v):B(v/v); $T_{0.0}$/100:0, $T_{5.0}$1100:0, $T_{35.0}$/0:100, $T_{50.0}$/0:100, $T_{51.0}$/100:0, and T60.0/100:0. Four related substances were detected in the laboratory crude Cinacalcet hydrochloride sample. The masses of detected peaks were 262.1 [(MH)$^+$], 304.2 [(MH)$^+$], 304.2 [(MH)$^+$], and 546.0 [(MH)$^+$].

The $^1$H NMR spectra were recorded on Bruker 300 MHz spectrometer using deuterated chloroform as solvent and tetramethylsilane (TMS) as internal standard.

Mass spectra were recorded on Waters Micro Mass-Quattro Micro API mass spectrometer equipped with a quadrupole mass analyzer. Detection of the ions was performed in electron spray ionization with positive ion mode. Spectra were acquired from m/z 60 to 800 in 0.1 amu steps with 10 numbers of scans.

FT-IR spectra were recorded for all the five degradation and process-related impurities on Perkin Elmer model-spectrum 100 instrument using KBr pellet method.

Solutions of all the impurities and Cinacalcet hydrochloride were prepared in diluents at a concentration of 10 μg/mL, and the UV-visible spectra were acquired. The UV absorption maxima of Cinacalcet and all the related substances were at approximately 210-220 nm. At 220 nm, the response factor for all the impurities relative to Cinacalcet was approximately 0.5 to 10.3, so detection at 220 nm was selected for method development.

The pKa value of Cinacalcet is 8.72, so it was decided that method development would occur in an acidic mobile phase. All the impurities possess varying polarities. For example, Impurity 7 is moderately polar, while impurities 10 and 11 are highly nonpolar. Hence, in any isocratic conditions, the impurity peaks and Cinacalcet were not well separated. Thus, the method development trials were performed on a gradient method.

In yet another aspect of the present invention, the separation of Cinacalcet and its impurities was critical because the impurities and Cinacalcet eluted very close to each other. In the preliminary trials, the peak shapes were found to be acceptable using Zorbax® SB Phenyl (250×4.6 mm, 5 μm) column with mobile phase-A (buffer 0.1% acetic acid, pH 5.5, adjusted with triethyl amine) and mobile phase-B (methanol) at 35° C. column oven temperature. When methanol was used as an organic modifier, the earlier eluting peaks were well separated, but it has been noticed that impurity 8 co-eluted with Cinacalcet. Furthermore, peaks of 10 and 11 were not eluted. To overcome this hurdle, further trials were performed using acetonitrile as an organic modifier in mobile phase-B. It was observed that non-polar impurities were eluted with acceptable peak symmetry; however, resolution between the closely eluting impurities was lost. Therefore, the combination of methanol, acetonitrile, and buffer in mobile phase-A and mobile phase-B were preferred.

To achieve the critical separation, the initial concentration of mobile phase-B is kept at 0% in the gradient program. The acceptable peak separation and peak shape was achieved by using mobile phase-A consisting of a mixture of buffer (0.1% v/v glacial acetic acid, pH 5.5 adjusted to with triethylamine), acetonitrile and methanol in the ratio of 45:35:20 (v:v:v), and mobile phase-B consisting of a mixture of acetonitrile and buffer in the ratio of 80:20 (v:v). The gradient condition was optimized as: (min)/A (v/v):B (v/v); $T_{0.01}/100:0$, $T_{5.0}/100:0$, $T_{10.0}/80:20$, $T_{25.0}/40:60$ $T_{35.0}/0:100$, $T_{50.0}/0:100$, $T_{53.0}/100:0$, with a post run time of 17 min. The flow rate and injection volumes were 1.0 mL/min and 10 μL, respectively. The selectivity was found to be >1.03 with resolution >1.70 for all the compounds (Cinacalcet and impurities).

Further studies were carried out on the effect of temperature, column flow rate, and pH of the buffer on the retention and separation of all the process impurities. Flow rate and temperature has no effect on the separation except the retention. Buffer pH played a major role in separating all the impurities. Effect of buffer pH was studied under the conditions described. The pH of the buffer is preferred at 5.50±0.05. A typical retention time of 3, 2, 7, 5, 9, 1 (Cinacalcet), 8, 10, and 11 were about 4.66, 5.63, 14.26, 17.45, 30.47, 22.24, 23.38, 27.27, and 40.40 min, respectively. The optimized method was validated as per ICH guidelines. The developed method was also applied to pharmaceutical formulations.

Validation of Reverse-Phase HPLC Method
Specificity (Selectivity)

The data on degradation studies revealed that the degradation products were well separated from the Cinacalcet and known related substances, and the peak purity data of Cinacalcet hydrochloride indicated that the compound was spectrally pure. The mass balance is a process of adding together the assay value and the levels of degradation products to see how closely these add up to 100% of initial value with due consideration of the margin of analytical error. The mass balance of stressed samples was close to 99.9%.

Linearity

Linearity test solutions for related substance were prepared by diluting the impurity stock solution to the required concentrations. The solutions were prepared at six concentrated levels from LOQ to 250% (LOQ, 50, 100, 150, 200, and 250%) with respect to the specification level of impurities. The data were subjected to statistical analysis using a linear-regression model. The RF of each impurity was determined using the slope of the Cinacalcet hydrochloride plot against each impurity plot.

Limits of Detection and Quantitation (LOD and LOQ)

The limit of detection and limit of quantitation were determined for Cinacalcet hydrochloride and for each of the related substances as per ICH Q2R1 guidelines from the standard deviation of the peak areas and slope of linearity data. The values of LOD and LOQ for Cinacalcet hydrochloride were 0.038 μg/mL and 0.116 μg/mL respectively, whereas for related substances in the ranges; 0.011-0.149 μg/mL and 0.033-0.451 μg/mL, respectively. The calculated LOQ concentrations of all the components were verified for precision by injecting six individual preparations of all related substances and Cinacalcet hydrochloride. The RSD of LOQ precision was in the range of 2.13-8.22%. These limits of quantification levels of the impurities were helpful for the process research work to control the impurities at the accepted level during the optimization of the process.

Precision

System precision for related substances determination was verified using system suitability solution, which was analyzed for six times and RSD of Cinacalcet hydrochloride, and all impurities peak areas were evaluated and found to be 0.28-4.90%.

Precision of the method was studied for repeatability (method precision) and intermediate precision. Repeatability was demonstrated by analyzing six separate Cinacalcet hydrochloride sample solutions that were prepared by spiking the related substances at specification level. The RSD (0.59-3.29%, n=6) for each related substance was evaluated. In the intermediate precision study, the similar procedure of repeatability was carried out by a different analyst, different instrument, and on a different day with different lot of same brand column. The percentage relative standard deviation of the results for related substances method was evaluated and found to be 0.71-4.90%. The results of the repeatability and intermediate precision were compared with each other. The over RSD (n=12) for percentage of impurities were found within the range of 1.28-9.30%.

Accuracy (Recovery)

Accuracy of the method for all the related substances was determined by analyzing Cinacalcet hydrochloride sample solutions spiked with all the related substances at four different concentration levels of LOQ, 50, 100, and 150% of each in triplicate at the specified limit. The recovery of all these related substances were found to be in-between the pre-defined acceptance criterion of 80.0-120.0%.

Stability of Analytical Solution

To determine the stability of the sample solution, the sample solutions of Cinacalcet hydrochloride spiked with related substances at specified levels were prepared and analyzed immediately after preparation and after different time intervals up to 8-days, while maintaining the sample cooler temperature at about room temperature. The results from these studies indicate, the sample solution was stable at room temperature and stable for 8-days at room temperature.

Mobile Phase Stability

To evaluate the mobile phase stability of the method, the Cinacalcet hydrochloride test sample spiked with related substances (i.e. impurities) at specification level was used. The Cinacalcet hydrochloride test sample was analyzed after 24 hrs and after 48 hrs by using the same mobile phase. The content of each impurity was evaluated and compared to the mean results of repeatability. The difference between the mean values (after 48 hrs) from the repeatability mean results is found to be below 10.0%. The studies indicated no effect on the determination of related substances and the selectivity after 48 hrs. Therefore, the mobile phase is stable for 48 hrs.

Robustness

To evaluate the robustness of the developed method, the chromatographic conditions were deliberately altered, and the resolution between closely eluting peak pair (i.e. Impurity 8 and Cinacalcet) was evaluated. The flow rate of the mobile phase was 1.0 mL/min. To study the effect of flow rate on the resolution, the same was altered by 0.1 units (i.e. 0.9 and 1.1 mL/min). The effect of column temperature on resolution was studied at 32° C. and 38° C., instead of at 35° C. All the other mobile phase components were held constant as described previously. In all the deliberate varied chromatographic conditions (flow rate and column temperature), the tailing factor of Cinacalcet hydrochloride was less than 1.2, and the resolution between any two peaks was always greater than 1.5, illustrating the robustness of the method.

Application of the Method

The method is specific and selective for determination of related substances in the formulation and bulk drug samples. The developed method is capable of quantitative analysis of Cinacalcet hydrochloride in the bulk drug and in a pharmaceutical dosage form in the presence of all these impurities.

The following experimental examples are illustrative of the invention but not limitative of the scope thereof.

EXAMPLES

Preparation of Cinacalet Hydrochloride

Example 1

Preparation of (1R)-1-(2-Naphthyl)-N-(Phenylmethylene) Thanamine Derivative of Formula (IV)

To a stirred solution of (R)-1-naphthyl ethylamine (5 gm) in ethanol (25 ml), benzaldehyde (3.71 gm) was added with stirring at 25-30° C. The reaction mass was stirred at 55-60° C. for 5-6 hours. Upon completion of this reaction by TLC, the reaction mass was cooled to 25-30° C., and then to 5-10° C. The reaction mixture was maintained for 30 minutes. The precipitated solid was filtered, washed with ethanol (10 ml), and dried under vacuum to yield 7.1 gm (94.67%) compound of formula (IV) as a white crystalline solid.

MS; m/z 260 (M$^+$+1). $^1$H NMR (CDCl$_3$): δ 8.44 (s, 1H), 8.27 (d, 1H), 7.80-7.87 (m, 5H), 7.48-7.51 (m, 3H), 7.41-7.42 (t, 3H), 5.37 (q, 1H), 1.74-1.76 (d, 3H). Related substances by HPLC 99.20%.

Example 2

Step 2: Preparation of Cinacalcet of Formula (I)

The solid compound of formula (IV) (5.0 gm) of step-1 and the 1-(bromopropyl)-3-(trifluoromethyl)benzene compound of the formula (V) (5.66 gm) were reacted in presence of potassium iodide (0.2 gm) at 120-130° C. till the completion of the reaction which was monitored by TLC (16-18 hours). The reaction mass was cooled to 25-35° C., diluted with water (50 ml) and acetonitrile (10 ml); the pH of the reaction mass was adjusted to 1-2 using concentrated hydrochloric acid and stirred for 60 min. The resulting reaction solution was extracted with n-heptane (50 ml). The aqueous layer was separated, basified with ammonia till pH 9-10 and then extracted with toluene (50 ml), with 10% sodium metabisulphite solution (50 ml) followed by water (25 ml) and distilled off the toluene layer to get Cinacalcet base as thick syrup; 4.9 gm (71.0%); HPLC purity 99.1%; chiral purity: 99.90%.

Example 3

Step 2: Preparation of Cinacalcet of Formula (I)

The solid compound of formula (IV) (5.0 gm) of step-1 and the 1-(bromopropyl)-3-(trifluoromethyl)benzene compound of the formula (V) (5.66 gm) were reacted in presence of potassium iodide (0.2 gm) at 120-130° C. till the completion of the reaction which was monitored by TLC (16-18 hours). The reaction mass was cooled to 25-35° C., diluted with water (50 ml), pH of the solution was adjusted to 1-2 using concentrated hydrochloric acid and stirred for 60 min. The resulting reaction solution was extracted with toluene (50 ml) and toluene layer was washed with 10% sodium metabisulphite solution (50 ml) followed by water. The toluene layer was separated and concentrated under vacuum to yield syrup, which is dissolved in the acetonitrile (10 ml) and water (50 ml). The pH of the resulting solution was adjusted to 1-2 using concentrated hydrochloric acid, washed the acidic aqueous layer with n-heptane (25 ml) and separated aqueous layer was basified with ammonia till pH 9-10. The mass was then extracted the toluene (50 ml), washed with water (25 ml) and distilled off the toluene layer to get Cinacalcet base as thick syrup; Yield 4.9 gm (71.0%); HPLC purity 99.1%; chiral purity: 99.90%.

Example 4

Step 2: Preparation of Cinacalcet of Formula (I)

The solid compound of formula (IV) (5.0 gm) of step-1,1-(bromopropyl)-3-(trifluoromethyl)benzene compound of the formula (V) (5.66 gm) in N-methyl-2-pyrrolidinone (25 ml) were heated at 130-140° C. till the completion of the reaction which was monitored by TLC (12 hours). The reaction mass was cooled 25-35° C., diluted with water (50 ml), the pH of the solution was adjusted to 1-2 using concentrated hydrochloric acid and stirred for 60 min. The resulting solution was extracted with toluene (50 ml), toluene layer was washed with 10% sodium metabisulphite solution (50 ml) and concentrated under vacuum to yield syrup. The syrup was dissolved in the acetonitrile (10 ml) and water (50 ml), the pH of the solution was adjusted to 1-2 using concentrated hydrochloric acid, and washed the acidic aqueous layer with n-heptane (25 ml). The aqueous layer was then basified with ammonia till pH 9-10 and then extracted the Cinacalcet base into toluene (50 ml). Toluene layer was washed with water (25 ml) and distilled off the toluene layer to get Cinacalcet base as thick syrup Yield: 4.45 gm (64.50%); HPLC purity 98.23%; Chiral purity: 99.89%.

Example 5

Step 2: Preparation of Cinacalcet of Formula (I)

The solid compound of formula (IV) (5.0 gm) obtained in step-1,1-(bromopropyl)-3-(trifluoromethyl)benzene compound of the formula (V) (5.66 gm) in N,N-dimethyl formamide (25 ml) were refluxed at 130-140° C. till the completion of the reaction which was monitored by TLC (12 hours) and the reaction mass was cooled to 25-35° C. The reaction solution was diluted with water (50 ml), the pH of the solution was adjusted to 1-2 using concentrated hydrochloric acid and stirred for 60 min. The resulting reaction solution was extracted with toluene (50 ml), washed with 10% sodium metabisulphite solution (50 ml) and concentrated under vacuum to yield syrup. The syrup was dissolved in the acetonitrile (10 ml) and water (50 ml), the pH of the solution was adjusted to 1-2 using concentrated hydrochloric acid and washed the acidic aqueous layer with n-heptane (25 ml). The aqueous layer was separated, basified with ammonia till pH 9-10, and extracted with toluene (50 ml). Toluene layer was washed with water (25 ml) and distilled off the toluene layer to get Cinacalcet base as thick syrup. Yield 3.44 gm (50.01%); HPLC purity 97.01%; chiral purity: 99.89%.

Example 6

Preparation of Cinacalcet Hydrochloride of Formula (VII)

Cinacalcet base Compound of formula (I) (5.0 gm) was dissolved in toluene (25 ml) and n-heptane (75 ml), and the pH of the solution was adjusted to 1-2 using concentrated hydrochloric acid at 25-30° C. and stirred for 30 minutes. The precipitated solid was filtered, washed with 10 ml n-heptane, and dried under vacuum to yield 5.1 gm (92.55%) of Cinacalcet hydrochloride; HPLC purity 99.80%; chiral purity: 99.95%.

Example 7

Preparation of Cinacalcet Hydrochloride of Formula (VII)

Cinacalcet base Compound of formula (I) (5.0 gm) was dissolved in diisopropylether (50 ml) and the pH of the solution was adjusted to 1-2 using concentrated hydrochloric acid at 25-30° C. The mass was stirred for 30 minutes, precipitated solid was filtered, washed with diisopropylether (10 ml) and dried under vacuum to yield 4.8 gm (86.48%) of Cinacalcet hydrochloride; HPLC purity 99.67%; Chiral purity: 99.92%.

Example 8

Preparation of Cinacalcet Hydrochloride of Formula (VII)

Solution of (1R)-1-naphthyl ethylamine (Formula II, 100 gm) and benzaldehyde (Formula III, 62.0 gm) was stirred at 25-30° C. for 1-2 hours. After completion of the reaction which was monitored by HPLC, N-methyl-2-pyrrolidinone (300 ml) was added to the reaction mass and stirred the mixture for 15-20 min. 1-(bromopropyl)-3-(trifluoromethyl) benzene (Formula V, 172 gm) was added to the resulting solution. The reaction mixture was further stirred and heated to at 130-140° C. for 12 hrs. After completion of the reaction (by HPLC), the reaction solution was diluted with water (1000 ml) and the pH of the solution was adjusted to 8-9 using aqueous ammonia, toluene (1000 ml) was added to the solution. The mixture was stirred and toluene layer was separated. The toluene layer were washed with water (1000 ml) followed by solution of 10% sodium metabisulphite (1000 ml×2). The toluene layer was diluted with water (1000 ml), adjusted pH of the solution to 0.5-2.0 using concentrated hydrochloric acid. The resulting reaction solution was stirred, separated aqueous layer and organic layer. Organic layer washed with water washed with water (1000 ml×2). The toluene layer was distilled off completely to obtain the thick syrup, which was further stirred in diisopropylether (600 ml) at 25-30° C. for 6 h isolated the solid by filtration. The obtained solid was suspended in ethyl acetate (500 ml), solution was heated at 55-60° C. for 30 min, cooled to 15-20° C., filter the obtained solid. The product was dried to afford Cinacalcet hydrochloride (Formula VII) as white crystalline solid. Yield of the compound VI 120 gm (52.10%). HPLC purity: 99.85%: Chiral Purity: 99.98% MS; m/z 358.79 (M$^+$+ 1). $^1$H NMR (DMSO-d$_6$): δ 10.12 (s, 1H), 9.43 (s, 1H), 8.26 (d, 1H), 8.08 (d, 1H), 7.99-8.03 (m, 2H), 7.60-7.63 (m, 3H), 7.53-7.54 (dt, 2H), 7.45-7.48 (dt, 2H). 5.32 (q, 1H), 2.93-2.96 (m, 1H), 2.69-2.74 (t, 3H), 1.97-2.07 (m, 2H), 1.68-1.71 (d, 3H).

Example 9

Purification Process for Cinacalcet Hydrochloride

Cinacalcet hydrochloride obtained from the example 8 was purified to improve chemical purity. The material (100 gm) was dissolved in a mixture of acetonitrile (200 ml) and water (1000 ml) and stirred and heated to 60-65° C. for 30-45 min. The resulting solution was cooled to 5-10° C., and maintained for 60 min. The crystalline solid obtained was filtered, and dried under vacuum (650-700 mm/Hg) to afford Cinacalcet hydrochloride of (Formula VII) as white crystalline solid. Yield: 90 gm (90.0%); HPLC purity: 99.95% and Chiral purity: 100.0%.

Examples

Preparation of Impurities

Impurities 7, 8, 9, 10 and 11 in pure form were prepared as follows:

Example 10

Preparation of (1R)—N-Benzyl-1-(1-Naphthyl)Ethanamine (7)

To a stirred solution of (1R)-1-(2-naphthyl)-N-(phenylmethylene) ethanamine (4, 10 g, 0.038 mol) in ethanol (200 mL) was added sodium cyanoborohydride (3.63 g, 0.057 mol) at 25-30° C. The reaction mass was further stirred at 45-50° C. for 5-6 h. Upon completion of the reaction (by TLC), the reaction mass was cooled, quenched with water (100 mL), and extracted with n-heptane (100 mL). The organic layer was separated, washed with water (100 mL), and concentrated under reduced pressure to provide a thick oil. The oil was dissolved in n-heptane (90 mL) and stirred, and the pH of the solution was adjusted to 1-2 using concentrated hydrochloric acid. The precipitated solid was filtered, washed with n-heptane (10 mL), and dried under vacuum to yield the title compound as a white crystalline solid. Yield: 8.2 g, (81.42%); HPLC purity: 99.10%; IR (KBr) cm$^{-1}$: 3445, 2965, 2759, 2728, 2682, 1596, 1457, 1378, 801, 781, 779; MS: m/z=262.07 [M+H]$^+$; $^1$H NMR (400 MHz, CDCl$_3$): δ=1.73-1.75 (d, J=8.8 Hz, 3H), 3.95-3.99 (br dd, 1H), 4.16-4.19 (br dd, 1H), 5.24-5.26 (q, J=8.8 Hz, 1H), 7.38-7.39 (m, 3H), 7.48-7.50 (t, 2H), 7.57-7.59 (m, 2H), 7.64-7.66 (d, 1H), 7.98-8.03 (m, 3H), 8.08-8.11 (d, J=9.2 Hz, 1H), 9.72 (bs, 1H), 10.48 (bs, 1H). $^{13}$C NMR (100 MHz, CDCl$_3$): δ=21.15 (CH$_3$), 48.34 (CH$_2$), 51.48 (CH), 121.35, 125.04, 125.9, 126.69, 128.52, 129.0, 129.11, 129.61, 130.21, 130.76, 132.11, 133.60.

Example 11

Preparation of (2E)-N-[(1R)-1-(1-Naphthyl) Ethyl]-3-[3-(Trifluoromethyl) Phenyl]Prop-2-En-1-Amine (8)

To a stirred solution of (1R)-1-naphthyl ethylamine (2, 10 g, 0.058 mol), was added benzaldehyde (3, 17.04 g, 0.064 mol) and maintained at 25-30° C. for 1-2 h. After the completion of reaction (by HPLC), N-methyl-2-pyrrolidinone (30 mL) was added followed by 1-[(1E)-3-bromopropyl-1en-1-yl]-3-(trifluoromethyl)benzene (5a, 17.04 g, 0.064 mol), and the temperature of the reaction mass was raised to 125-130° C. and maintained for 12 h. After completion of the reaction (by HPLC), the reaction mass was quenched with water (100 mL); the pH was adjusted to 8-9 using aqueous ammonia, and the solution was extracted with toluene (100 mL). The toluene layer was separated, washed with water (100 mL) followed by an aqueous solution of 10% sodium metabisulphite (100 mL×2). Water (100 mL) was added to the toluene layer, and the pH of the solution was adjusted to 0.5-1.5 using concentrated hydrochloric acid, and the resulting reaction solution was stirred for 10-15 min. Organic layer was separated, washed with water (100 mL×2), and concentrated under reduced pressure to provide a thick syrup. The syrup was then dissolved in n-heptane (60 mL) and stirred for 2-3 h; the obtained solid was filtered. This solid was suspended in ethyl acetate (50 mL); the suspension was heated at 55-60° C. for 30 min and cooled to 15-20° C.; the obtained solid was filtered, washed with ethyl acetate, and dried to afford compound the title compound as a white crystalline solid. Yield: 13.80 g (60%); HPLC purity: 90.20%; Chiral Purity: 99.9%; IR (KBr) cm$^{-1}$: 2961, 2925, 2853, 1734, 1595, 1448, 1331, 1164, 1124, 1072, 799, 778, 696; MS: m/z=356.1 [M+H]$^+$; $^1$H NMR (400 MHz, DMSO-d$_6$): δ=1.46-1.48 (d, 3H), 3.32-3.35 (d, J=7.6 Hz, 2H), 4.82 (q, 1H), 6.47-6.52 (dt, J=18.0 and 7.6 Hz, 1H), 6.57-6.61 (d, J=16.0 Hz, 1H), 7.49-7.54 (m, 6H), 7.68-7.70 (d, J=8.0 Hz, 1H), 7.77-7.79 (d, J=8.0 Hz, 1H), 7.83-7.85 (d, J=8 Hz, 1H), 7.93-7.95 (dd, J=8.0 Hz, 1H), 8.23-8.25 (dd, J=8.0 and 7.2 Hz, 1H); $^{13}$C NMR (100 MHz, DMSO-d$_6$): δ=20.19 (CH$_3$), 46.61 (CH$_2$), 51.44 (CH), 122.62 (CH), 122.72 (CH), 122.93, 124.69, 125.48 (CF$_3$), 125.63, 126.15, 126.87, 128.97, 129.37, 129.69, 129.90, 130.25, 130.36, 133.41, 134.03, 134.61.

Example 12

Preparation of 3-(3-Methylphenyl)-N-[(1R)-1-(1-Naphthyl) Ethyl]Propan-1-Amine (9)

To a stirred solution of (1R)-1-naphthyl ethylamine (2, 10 g, 0.058 mol) was added the benzaldehyde (3, 17.04 g, 0.058 mol) and stirred at 25-30° C. for 1-2 h. After completion of the reaction (by HPLC) N-methyl-2-pyrrolidinone (30 mL) was added to the mixture and stirred for 15-20 min followed by addition of 1-(3-bromopropyl)-3-methylbenzene (18.68 g, 0.087 mol). The temperature of reaction mass was raised to 125-130° C. and maintained until completion of the reaction (by HPLC). The reaction mass was quenched with water (100 mL), pH of the resulting solution was adjusted to 8-9 using aqueous ammonia, and the solution was extracted with toluene (100 mL). The toluene layer was separated, washed with water (100 mL) followed by 10% sodium metabisulphite (100 mL×2). Water (100 mL) was added into toluene layer, and the pH of the solution was adjusted to 0.5-1.5 using concentrated hydrochloric acid. The resulting solution was stirred, and the layers were separated. The organic layer was washed with water (100 mL×2) and concentrated under reduced pressure to provide thick syrup. Syrup was dissolved in n-heptane (60 mL) and stirred for 2 h, and the solid obtained was filtered. The wet solid was suspended in ethyl acetate (50 mL); the solution was heated at 55-60° C. for 30 min, cooled to 15-20° C., filtered, washed with ethyl acetate, and dried to afford des(trifluorocinacalcet), the title compound, as a white crystalline solid. Yield: 11.0 g (55.92%); HPLC purity: 99.60%; Chiral Purity: 99.90%; IR (KBr) cm$^{-1}$: 3435, 3006, 2962, 2945, 2798, 1588, 1455, 799, 771, 702; MS: m/z=304.2 [M+H]$^+$; $^1$H NMR (400 MHz, DMSO-d$_6$): δ=1.66-1.68 (d, 3H), 1.93-1.96 (m, 2H), 2.22 (s, 3H), 2.52-2.54 (m, 2H), 2.71-2.74 (dt, 1H), 2.90-2.94 (dt, 1H), 5.29-5.31 (q, 1H), 6.89-6.97 (dd, J=8.0 Hz and 3.0 Hz, 3H), 7.11-7.13 (t, J=8.0 Hz, 1H), 7.59-7.63 (dd, J=8.0 Hz and 3.0 Hz, 3H), 7.97-8.02 (m, 3H), 8.23-8.25 (d, J=8.0 Hz, 1H), 9.24 (bs, 1H), 9.84 (s, 1H); $^{13}$C NMR (100 MHz, DMSO-d$_6$): δ=20.13 (CH$_3$), 21.02 (CH$_3$), 27.16 (CH$_2$), 31.92 (CH$_2$), 44.88 (CH$_2$), 52.07 (CH), 122.68, 124.51, 125.25, 125.62, 126.19, 126.64, 126.98, 128.64, 128.89, 130.36, 133.39, 134.22, 137.36, 140.59.

Example 13

Preparation of 3-(3-(Trifluoromethyl)Cyclohexyl)-N—((R)-1-(Naphthalen-1-Yl) Ethyl)Propan-1-Amine (10)

(2E)-3-[3-(Trifluoromethyl)phenyl]acrylic acid (100 g, 0.462 mol), methanol (1000 mL), and 10% Pd/C (25.0 g, 50% wet) were added into an autoclave, and hydrogen pressure of 5 kg/cm$^2$ was applied; the reaction was maintained at 50-55° C. for 8 days. The catalyst was filtered, and solvent was removed under reduced pressure to obtain 3-[3-trifluoromethyl)cyclohexyl]propanoic acid (98.0 g) as an oil. The oil was then treated with 2 (67.68 g, 0.395 mol) in toluene (670 mL) at 110° C. for 16-18 h in the presence of boric acid (1.4 g, 0.022 mol) under azeotropic conditions. After completion of the reaction (by TLC), the reaction mass was cooled to 25-30° C., and washed with 2N hydrochloric acid solution (670 mL) followed by 10% aqueous solution of sodium bicarbonate (670 mL) and water (500 mL). The organic layer was separated and concentrated under reduced pressure to yield 114.0 g of amide compound 12 (Scheme 7). To a cooled solution of amide 12 in tetrahydrofuran (1700 mL) was added NaBH$_4$ (89.62 g, 3.258 mol) lotwise at −5 to 0° C., followed by slow addition of BF$_3$-etherate (349.55 g, 5.14 mol). Reaction mass was heated to 50-55° C., maintained for 5-6 h, and quenched over 2N hydrochloric acid solution (456 mL). The resulting reaction mass was distilled out atmospherically below 70° C. to remove THF and cooled to 25-30° C.; the pH of the reaction mass was adjusted to 8-9 using aqueous ammonia. The reaction mass was extracted with toluene (1140 mL), the toluene layer was washed with water (500 mL) and concentrated to get crude 10 as oil. The obtained crude oil was purified by column chromatography on silica gel (70 mm×60 cm column) using neat chloroform as the elution solvent to afford the title compound as a white solid. (see Scheme 7). Yield: 13.0 g; HPLC purity: 86.3%; Chiral Purity: 99.9%; IR (KBr): cm$^{-1}$ 3434, 2938, 2859, 2736, 1587, 1453, 1256, 1170, 1096, 800, 778; MS: m/z=364.10 [M+H]$^+$; $^1$H NMR (400 MHz, DMSO-d$_6$): δ=0.82-0.88 (m, 2H), 1.14-1.22 (m, 4H), 1.48-1.52 (t, 4H), 1.49-1.52 (d, 3H), 1.72-1.86

(m, 4H), 2.50-2.56 (t, 2H), 4.63-4.64 (q, 1H), 7.45-7.48 (m, J=8.0 and 3.0 Hz, 3H), 7.62-7.64 (d, J=8.0 Hz, 1H), 7.73-7.75 (d, J=8.0 Hz, 1H), 7.86-7.88 (d, J=8.0 Hz, 1H), 8.16-8.18 (d, J=8.0 Hz, 1H); $^{13}$C NMR (100 MHz, DMSO-$d_6$): δ=20.03 (CH$_3$), 22.70, 23.59, 24.46, 28.79, 30.94, 31.32, 33.22, 34.91, 45.42, 52.01, 122.65, 124.41, 125.60, 126.18, 126.96, 128.92 (CF$_3$), 130.31, 133.38, 134.27.

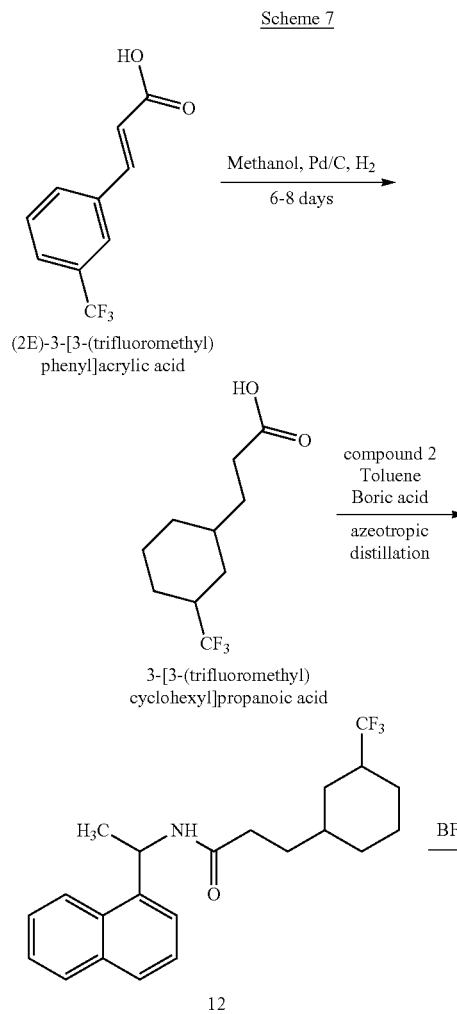

Example 14

Preparation of (1-Naphthalen-1-Yl-Ethyl)-N,N-Bis-[3-(3-Trifluoromethylphenyl)-Propyl]Amine (11)

To a stirred solution of Cinacalcet hydrochloride (1, 10 g, 0.028 mol) in toluene (150 mL) was added potassium carbonate (7.74 g, 0.056 mol) followed by 1-(3-bromopropyl)-3-(trifluoromethyl)benzene (5, 14.95 g, 0.056 mol) under stirring at 25-30° C. The reaction mass was heated and stirred at 110-111° C. for 48 h. Upon completion of the reaction (by TLC), the reaction mass was cooled and quenched with water (100 mL). The organic layer was separated, washed with water (100 mL), and concentrated under reduced pressure to obtain a thick oil. The crude oil was then purified by column chromatography on silica gel (70 mm×60 cm column) by eluting with chloroform to afford the title compound as a thick transparent oil. Yield: 10.50 g (69.03%); HPLC purity: 91.22%; IR (NaCl) cm$^{-1}$: 3441, 3049, 2940, 2861, 1596, 1492, 1449, 1331, 900, 702, 661; MS: m/z=544.0 [M+H]$^+$; $^1$H NMR (400 MHz, CDCl$_3$): δ=1.35-1.37 (d, 3H), 1.57-1.63 (m, 4H), 2.42-2.46 (t, 4H), 2.52-2.55 (t, 4H), 4.60-4.62 (m, 1H), 7.23-7.25 (d, J=8.0 Hz, 1H), 7.32 (s, 2H), 7.37-7.41 (t, 3H), 7.47-7.51 (m, 6H), 7.76-7.78 (d, J=8.0 Hz, 1H), 7.87-7.89 (dd, 1H), 8.42-8.44 (d, J=8.0 Hz, 1H). $^{13}$C NMR (100 MHz, DMSO-$d_6$): δ=15.46 (CH$_3$), 29.38 (CH$_2$), 32.99 (CH$_2$), 50.03 (CH$_2$), 56.90 (CH), 122.68, 122.72, 122.76, 123.37, 124.78, 124.83, 124.86, 124.91, 125.58, 125.68, 125.72 (CF$_3$), 128.88, 129.28, 129.33, 129.40, 129.49, 129.58, 129.60, 129.91, 132.06, 132.63, 134.04, 140.62, 144.01.

What is claimed is:

1. A method of preparing a compound of Formula (I) or a salt thereof, comprising reacting a compound of Formula (IV) with a compound of Formula (V) to produce the compound of Formula (I),

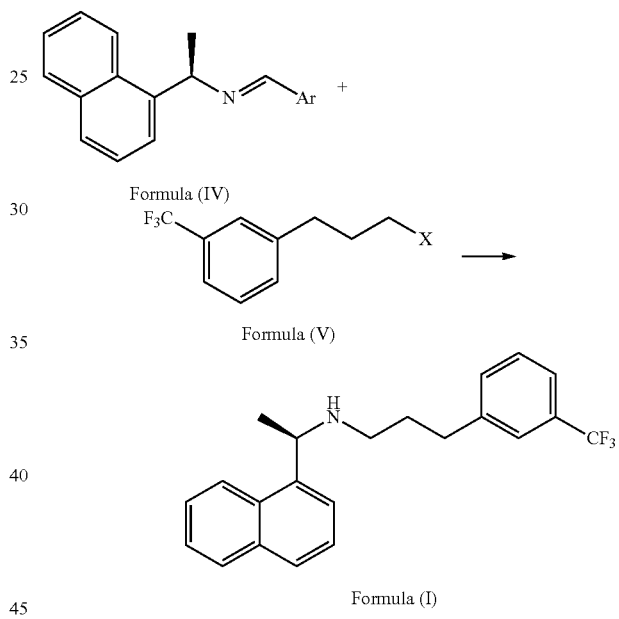

wherein
Ar is benzyl-, phenyl- or naphthyl-, which may be mono- or di- or poly substituted with alkyl, aryl, alkoxy, amino, hydroxyl, halogen, and nitro groups, and X is chloro, bromo, or iodo.

2. The method of claim 1, wherein
(a) the reaction of the compound of Formula (IV) with the compound of Formula (V) (1-(3-halopropyl)-3-(trifluoromethyl)benzene) forms an iminium salt of Formula (VI):

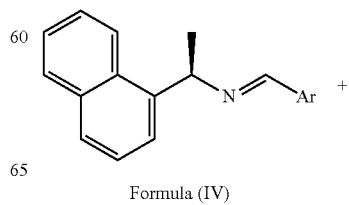

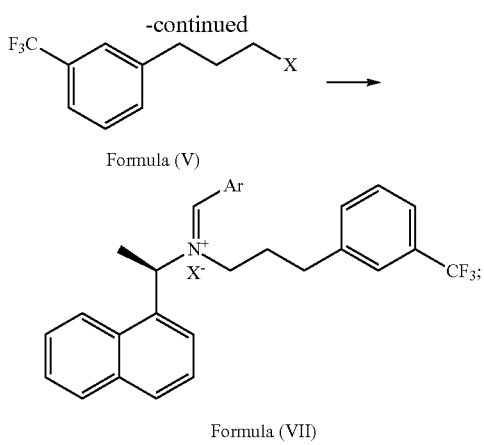

Formula (V)

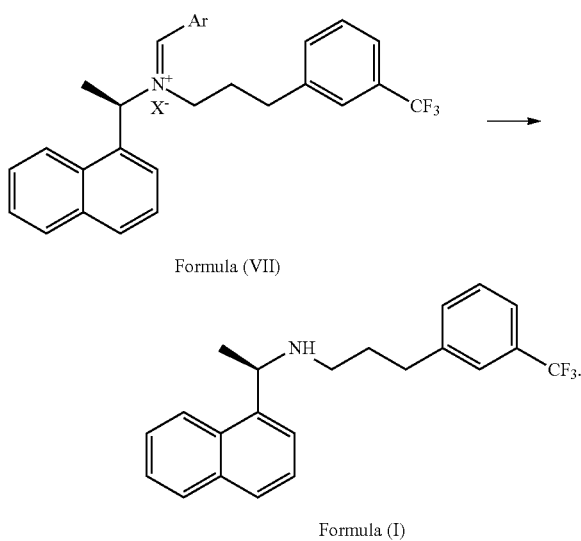

Formula (VII)

and (b) the iminium salt of Formula (VI) is treated with water and/or acid solution to obtain the compound of Formula (I):

Formula (VII)

Formula (I)

3. The method of claim 1, wherein the compound of Formula (IV) and the compound of Formula (V) are reacted at a temperature of 80 to 180° C.

4. The method of claim 3, wherein the reaction is carried out in the presence of a solvent.

5. The method of claim 4, wherein the solvent is selected from an organic solvent, an inorganic solvent, or mixtures thereof.

6. The method of claim 4, wherein the reaction is carried out at a reflux temperature of the solvent.

7. The method of claim 5, wherein the organic solvent is selected from C2-C8 aliphatic amides, cyclic amides, dimethylsulfoxides, hydrocarbon solvents, alcoholic solvents, ether solvents, and mixtures thereof.

8. The method of claim 7, wherein the C2-C8 aliphatic amide is selected from N,N-dimethylacetamide, dimethylformamide, hexamethylphosphoramide, and the like.

9. The method of claim 7, wherein the cyclic amide is selected from 1,3-dimethyl-2-imidazolidinone (DMI), N-methyl-2-pyrrolidinone (NMP), and the like.

10. The method of claim 7, wherein the hydrocarbon solvents are selected from toluene, xylene, and the like.

11. The method of claim 7, wherein the alcoholic solvents are selected from methanol, ethanol, propanol, butanol, and the like.

12. The method of claim 7, wherein the ether solvent is diglymes.

13. The method of claim 7, wherein the organic solvent is N-methyl-2-pyrolidnone.

14. The method of claim 5, wherein the inorganic solvent comprises an ionic liquid selected from 1-ethyl-3-methyl imidazolium ethylsulfate, [hmim]$BF_4$, [hbim]Br, [hbim]Cl, [hbim]$BF_4$, [hbim]$PF_6$, [bbim]Br, [bbim]Cl, [bbim]$ClO_4$, [bbim]$BF_4$, [bmim]$PF_6$, [bmim]$BF_4$, and the like, and mixtures thereof.

15. The method of claim 2, further comprising the addition of a catalyst.

16. The method of claim 15, wherein the catalyst is selected from potassium iodide (KI), sodium iodide (NaI), or phase transfer catalysts selected from n-benzylcinchonidinium chloride, benzyltributylammonium chloride, 3-ethyl-5-(2-hydroxyethyl)-4-methylthiazolium bromide, phenyltrimethylammonium chloride, tetrabutylammonium bromide, tetrabutylammonium chloride, tricaprylmethylammonium chloride, tetrabutylammonium iodide, and the like, or combinations thereof.

17. The method of claim 3, wherein the reaction is carried out at a temperature of 120 to 150° C.

18. The method of claim 2, wherein the compound of Formula (V) is selected from 1-(3-chloropropyl)-3-(trifluormethyl)benzene, 1-(3-bromopropyl)-3-(trifluormethyl)benzene, or 1-(3-iodopropyl)-3-(trifluoromethyl)benzene.

19. The method of claim 2, wherein the acid solution comprises concentrated hydrochloric acid.

* * * * *

UNITED STATES PATENT AND TRADEMARK OFFICE
CERTIFICATE OF CORRECTION

| | | |
|---|---|---|
| PATENT NO. | : 8,969,623 B2 | Page 1 of 1 |
| APPLICATION NO. | : 14/052116 | |
| DATED | : March 3, 2015 | |
| INVENTOR(S) | : Vijayavitthal Thippanachar Mathad et al. | |

It is certified that error appears in the above-identified patent and that said Letters Patent is hereby corrected as shown below:

On The Title Page, item (73) Assignee: "Amneal Pharamceuticals, LLC, Bridgewater, NJ (US)" should be changed to --Amneal Pharmaceuticals, LLC, Bridgewater, NJ (US); Megafine Pharma (P) LTD., Mumbai (IN)--.

Signed and Sealed this
Eighth Day of December, 2015

Michelle K. Lee
*Director of the United States Patent and Trademark Office*